(12) United States Patent
Boyette et al.

(10) Patent No.: US 10,653,729 B2
(45) Date of Patent: May 19, 2020

(54) DELIVERY SYSTEM AND PROBIOTIC COMPOSITION FOR ANIMALS AND PLANTS

(71) Applicant: NCH Corporation, Irving, TX (US)

(72) Inventors: Scott Martell Boyette, Irving, TX (US); Judith Gayle Pruitt, Mesquite, TX (US); John Knope, Flower Mound, TX (US); Adrian Denvir, Richardson, TX (US); Charles Greenwald, Irving, TX (US); Alex Erdman, Irving, TX (US)

(73) Assignee: NCH Corporation, Irving, TX (US)

( * ) Notice: Subject to any disclaimer, the term of this patent is extended or adjusted under 35 U.S.C. 154(b) by 236 days.

(21) Appl. No.: 14/524,858

(22) Filed: Oct. 27, 2014

(65) Prior Publication Data

US 2015/0118203 A1    Apr. 30, 2015

Related U.S. Application Data

(60) Provisional application No. 61/895,775, filed on Oct. 25, 2013.

(51) Int. Cl.
| | | |
|---|---|---|
| *A61K 35/745* | (2015.01) | |
| *A01G 22/00* | (2018.01) | |
| *A01K 7/02* | (2006.01) | |
| *A61D 7/00* | (2006.01) | |
| *A23K 10/18* | (2016.01) | |
| *A01K 5/00* | (2006.01) | |
| *A01K 7/00* | (2006.01) | |
| *A61K 35/741* | (2015.01) | |
| *A61K 35/742* | (2015.01) | |
| *A61K 35/744* | (2015.01) | |
| *A61K 35/00* | (2006.01) | |

(52) U.S. Cl.
CPC ............ *A61K 35/745* (2013.01); *A01G 22/00* (2018.02); *A01K 5/00* (2013.01); *A01K 7/00* (2013.01); *A01K 7/02* (2013.01); *A23K 10/18* (2016.05); *A61D 7/00* (2013.01); *A61K 35/741* (2013.01); *A61K 35/742* (2013.01); *A61K 35/744* (2013.01); *A61K 2035/115* (2013.01)

(58) Field of Classification Search
CPC .. A61K 35/745; A61K 35/741; A61K 35/742; A61K 35/744; A61K 2035/115; A23K 10/18; A01K 5/00; A01K 7/00; A01K 7/02; A61D 7/00
USPC ...................................................... 424/93.45
See application file for complete search history.

(56) References Cited

U.S. PATENT DOCUMENTS

| | | |
|---|---|---|
| 4,314,995 A | 2/1982 | Hata et al. |
| 4,840,792 A | 6/1989 | Joulain et al. |
| 4,872,985 A | 10/1989 | Dinges |
| 4,910,024 A | 3/1990 | Pratt |
| 4,919,936 A | 4/1990 | Iwanami et al. |
| 4,999,193 A | 3/1991 | Nguyen |
| 5,093,121 A | 3/1992 | Kvanta et al. |
| 5,154,594 A | 10/1992 | Gamlen |
| 5,292,523 A | 3/1994 | Kono et al. |
| 5,320,256 A | 6/1994 | Wood |
| 5,501,857 A | 3/1996 | Zimmer |
| 5,702,604 A | 12/1997 | Yamasaki et al. |
| 5,821,112 A | 10/1998 | Botto et al. |
| 5,968,569 A | 10/1999 | Cavadini et al. |
| 6,254,910 B1 | 7/2001 | Paluch |
| 6,308,658 B1 | 10/2001 | Steckel |
| 6,312,746 B2 | 11/2001 | Paluch |
| 6,335,191 B1 | 1/2002 | Kiplinger et al. |
| 6,382,132 B1 | 5/2002 | Steckel et al. |
| 6,461,607 B1 | 10/2002 | Farmer |

(Continued)

FOREIGN PATENT DOCUMENTS

| | | |
|---|---|---|
| EP | 0826311 | 3/1998 |
| EP | 0885557 | 8/2004 |

(Continued)

OTHER PUBLICATIONS

He et al. (Effects of Trehalose, Glycerin and NaCl on the Growth and Freeze-Drying of Lactobacillus Acidophilus. Information Technology and Agricultural Engineering. 2012; 967-971).*
El-Mougy (Application of Fungicides Alternatives as Seed Treatment for Controlling Root Rot of Some Vegetables in Pot Experiments. Advances in Life Sciences 2012, 2(3):57-64).*
Yeo et al (Antihypertensive Properties of Plant-Based Prebiotics. Int. J. Mol. Sci. 2009, 10, 3517-3530).*
Chorawala, M. R., P. M. Oza, G. B. Shah, 2011. Probiotics, Prebiotics and Synbiotics: A Health Benefit Supplement. Research Journal of Pharmaceutical, Biological and Chemical Sciences vol. 2 (3): 1101-1111.
Sekhon, B. S. and J. Saloni. 2010. Prebiotics, probiotics and synbiotics: an overview. Journal of Pharmaceutical Education and Research. 1:13-36.

(Continued)

*Primary Examiner* — Sharmila G Landau
*Assistant Examiner* — Natalie M Moss
(74) *Attorney, Agent, or Firm* — Ross Barnes LLP; Robin L. Barnes

(57) ABSTRACT

Probiotic compositions that comprise one or more bacteria species in spore form, a thickener to form a stabilized suspension and to preferably act as a prebiotic, one or more acids or salts of acids, and optionally a water activity reducer. A system for delivering probiotic compositions by gravity feed or non-contact pump to a point of consumption by a plant or animal, preferably in conjunction with acidified drinking water, comprising a collapsible container with attachable tubing that prevent contamination of the probiotic composition within the container. Delivery may be actuated in response to a timer, motion detector, fluid level sensor, RFID tag, or other mechanism to periodically or continuously dispense a dosage of probiotic composition directly to the soil surrounding a plant or to the water or feed for an animal. A method for increasing beneficial bacteria in an animal's GIT comprises adding probiotics to acidified drinking water.

32 Claims, 6 Drawing Sheets

(56) References Cited

U.S. PATENT DOCUMENTS

| | | | |
|---|---|---|---|
| 6,498,137 B1 * | 12/2002 | Schalitz | C11D 1/62 510/199 |
| 6,723,076 B1 | 4/2004 | Strobel | |
| 6,827,957 B2 | 12/2004 | Paluch et al. | |
| 6,849,256 B1 | 2/2005 | Farmer | |
| 7,081,361 B2 | 7/2006 | Pearce, III et al. | |
| 7,485,466 B2 | 2/2009 | Jenkins et al. | |
| 7,635,587 B2 | 12/2009 | Pearce, III et al. | |
| 7,670,845 B2 | 3/2010 | Wenzel et al. | |
| 7,713,726 B2 | 5/2010 | Farmer | |
| 7,754,469 B2 | 7/2010 | Baltzley et al. | |
| 8,025,847 B2 | 9/2011 | Fouarge et al. | |
| 8,025,874 B2 | 9/2011 | Bellot et al. | |
| 8,062,902 B2 | 11/2011 | Mestrallet | |
| 8,093,040 B2 | 1/2012 | Pearce, III et al. | |
| 8,192,733 B2 | 6/2012 | Cobb et al. | |
| 8,277,799 B2 | 10/2012 | Farmer | |
| 8,349,337 B1 * | 1/2013 | Farmer | A23L 1/0528 424/247.1 |
| 8,404,227 B2 | 3/2013 | Bellot et al. | |
| 8,506,951 B2 | 8/2013 | Rehberger et al. | |
| 8,540,981 B1 | 9/2013 | Wehnes et al. | |
| 8,551,762 B2 | 10/2013 | Fleming et al. | |
| 8,647,690 B2 * | 2/2014 | Corrigan | A23K 1/004 426/302 |
| 2003/0031659 A1 * | 2/2003 | Farmer | A61K 31/496 424/93.45 |
| 2003/0165472 A1 | 9/2003 | McGrath et al. | |
| 2006/0093591 A1 * | 5/2006 | Farmer | A23L 33/135 424/93.45 |
| 2008/0107699 A1 | 5/2008 | Spigelman et al. | |
| 2009/0041898 A1 * | 2/2009 | Garbolino | A23D 7/0053 426/61 |
| 2009/0186057 A1 * | 7/2009 | Farmer | A01N 63/00 424/404 |
| 2011/0189132 A1 | 8/2011 | Garner et al. | |
| 2011/0230345 A1 * | 9/2011 | Snyder | C12R 1/07 504/101 |
| 2011/0256216 A1 | 10/2011 | Lefkowitz | |
| 2012/0052152 A1 | 3/2012 | Armentrout | |
| 2012/0100094 A1 * | 4/2012 | Reuter | C12N 1/04 424/76.6 |
| 2013/0017174 A1 | 1/2013 | Hargis et al. | |
| 2013/0092087 A1 | 4/2013 | Bachman et al. | |
| 2013/0202562 A1 | 8/2013 | Wood | |
| 2014/0220662 A1 | 8/2014 | Hashman | |
| 2015/0118203 A1 | 4/2015 | Boyette et al. | |

FOREIGN PATENT DOCUMENTS

| | | | |
|---|---|---|---|
| WO | WO2000033854 | 6/2000 | |
| WO | WO2002051264 | 7/2002 | |
| WO | WO2006002495 | 1/2006 | |
| WO | WO2008071930 | 6/2008 | |
| WO | WO2009/126473 | * 3/2009 | A01N 25/26 |
| WO | WO2009040445 | 4/2009 | |
| WO | WO2009/126473 | * 10/2009 | A01N 25/26 |
| WO | WO2009117790 | 10/2009 | |
| WO | WO2010003255 | 1/2010 | |
| WO | WO2010020639 | 2/2010 | |
| WO | WO 2010045547 | * 4/2010 | A23L 1/105 |
| WO | WO2010066012 | 6/2010 | |
| WO | WO2010079104 | 7/2010 | |
| WO | WO2010088744 | 8/2010 | |
| WO | WO2010142004 | 12/2010 | |
| WO | WO2012079973 | * 11/2011 | A23L 1/00 |
| WO | WO2012027214 | 3/2012 | |
| WO | WO2012108830 | 8/2012 | |
| WO | WO2012167882 | 12/2012 | |
| WO | WO2014083177 | 6/2014 | |

OTHER PUBLICATIONS

Patterson, J.A., K. M. Burkholder. 2003. Application of prebiotics and probiotics in poultry production. Poultry Science 82:627-631.
ADM Alliance Nutrition—DFM Fact Sheet—Attachement—Body of text—p. 2.
Casula, G and S. Cutting. 2002. Bacillus Probiotics: Spore Germination in the Gastrointestinal Tract. American Society for Microbiology. vol. 68, No. 5: 2344-2352.
Amerah, A.M., C. J. van Rensburg, P. W. Plumstead, C. Kromm, and S. Dunham. 2013. Effect of feeding diets containing a probiotic or antibiotic on broiler performance, intestinal mucosa-associated avian pathogenic E. coli and litter water-soluble phosphorus. Journal of Applied Animal Nutrition.
Sutton, A.L. et al., Potential for Reduction of Odorous Compounds in Swine Manure Through Diet Modification, J. Anim. Sci. 1999, 77:430-439.
Davis M.E. et al, Effect of a Bacillus-based direct-fed microbial feed supplement on growth performance and pen cleaning characteristics of growing-finishing pigs, J. Anim. Sci. 2008, 86:1459-1467.
Sutton, A. L., K. B. Kephart, M. W. A. Verstegen, T. T. Canh, and P. J. Hobbs. 1999. Potential for reduction of odorous compounds in swine manure through diet manipulation. Journal of Animal Science 77:430-439.
Davis, M. E., T. Parrott, D. C. Brown, B. Z. de Rodas, Z. B. Johnson, C. V. Maxwell, T. Rehberger. 2008. Effect of a Bacillus-based direct-fed microbial feed supplement on growth performance and pen cleaning characteristics of growing-finishing pigs. Journal of Animal Science 86:1459-1467.
Acidified water—Acid-Lac Swine Poultry Data Sheet, 2011.
Acidified water—Kern-San Swine Poultry Spec Sheet, 2011.
Scientific opinion on the safety and efficacy of Bactocell (Pediococcus acidilactici) as a feed additive for use in water for drinking for weaned piglets, pigs for fattening, laying hens and chickens for fattening. EFSA Journal 2012: 10(7):2776.
Use of probiotics in aquaculture, EPA Position Paper, 2012.
Safe Feeding with Lupro-Grain and Amasil NA—product brochure available from BASF Chemical Company, published at least as early as 2011, Retrieved from the Internet on Feb. 16, 2015 at <URL: http://www.basfanimalnutrition.de/downloads/an_safe_feeding_en.pdf and http://www.basfanimalnutrition.de/en/news_2008_09_09.php>.
Supporting More Sustainable Livestock Production Luprosil & Amasil Less Spoilage, Improved Hygiene, product brochure from BASF Chemical Company, believed published at least as early as 2011, Retrieved from the Internet on Feb. 16, 2015 at <URL: http://www.newtrition.basf.com/web/global/de/function/conversions:/publish/content/microsites/animal-nutrition/Sustainability_Contribution/assets/Luprosil_Amasil.pdf>.
Activate & Activate WD Max Product Information available from Novus, believed published at least as early as 2011, Retrieved from the Internet on Feb. 16, 2015 at http://novusintqa.enlivenhq.com/Products/activate#fndtn-activatewdmax.
Bactocell Drink is Now Authorized in Europe as a Feed Additive for Swine and Poultry, news release from Lallemand Animal Nutrition, published May 15, 2013, Retrieved from the Internet on Feb. 16, 2015 at <URL: http://lallemandanimalnutrition.com/news/bactocell-drink-is-now-authorized-in-europe-as-a-feed-additive-for-swine-and-poultry/>.
Bactocell Drink on-tracks for EU authorization as a feed additive for use in drinking water for swine and poultry, news release from Lallemand Animal Nutrition, published Aug. 29, 2012, Retrieved from the Internet on Feb. 16, 2015 at <URL: http://lallemandanimalnutrition.com/news/bactocell-drink-on-tracks-for-eu-authorization-as-a-feed-additive-for-use-in-drinking-water-for-swine-and-poultry/>.
Feed Preservation with formic acid from BASF, product information available from BASF Chemical Company, believed to be

(56) References Cited

OTHER PUBLICATIONS published at least as early as 2011, Retrieved from the Internet on Feb. 16, 2015 at <URL: http://www.intermediates.basf.com/chemicals/formic-acid/feed-preservation>.

The Great Preserver—Propionic Acid protects food and animal feed from mold—rising demand, product information available from BASF Chemical Company, believed to be published at least as early as 2011, Retrieved from the Internet on Feb. 16, 2015 at <URL: http://www.intermediates.basf.com/chemicals/topstory/propionsaeure>.

Organic Acids, product information available from BASF Chemical Company, believed to be published at least as early as 2011, Retrieved from the Internet on Feb. 16, 2015 at <URL: http://www.animal-nutrition.basf.com/web/global/animal-nutrition/en_GB/Products/OrganicAcids/index>.

Poultry Product Quality—product information regarding BioPlus available from Chr. Hansen, believed to be published at least as early as 2011, Retrieved from the Internet on Feb. 16, 2015 at <URL: http://www.chr-hansen.com/animal-probiotics-and-silage-inoculants/probiotics-for-poultry/poultry-product-quality>.

European Food Safety Authority Scientific Opinion on the Safety and Efficacy of BioPlus 2B, published in the EFSA Journal 2011; 9(9):2356, Retrieved from the Internet on Feb. 16, 2015 at <URL: http://www.efsa.europa.eu/sites/default/files/scientific_output/files/main_documents/2356.pdf>.

Biotic for Shrimp—product information available from Biopharmachemie, believed to be published at least as early as 2011, Retrieved from the Internet on Feb. 16, 2015 at <URL: http://biopharmachemie.com/product/products-for-shrimp/biotic-for-shrimp.html>.

Biozyme for Shrimp—product information available from Biopharmachemie, believed to be published at least as early as 2011, Retrieved from the Internet on Feb. 16, 2015 at <URL: http://biopharmachemie.com/product/products-for-shrimp/biozyme-for-shrimp.html>.

Biotic for Poultry and Swine—product information available from Biopharmachemie, believed to be published at least as early as 2011, Retrieved from the Internet on Feb. 16, 2015 at <URL: http://www.biopharmachemie.com/product/products-for-livestock/biotic.html>.

Dosatron Water Powered Dosing Technology D 25 Range—product brochure available from Dosatron International, published 2007, Retrieved from the Internet on Feb. 16, 2015 at <URL: https://bd.dosatron.com/Products_Produits/RangeSheets_FichesGamme/D25/Rangesheet_FichesGamme_D25_EN.pdf>.

Delivering superior swine performance—product information on VevoVitall available from DSM, believed to be published at least as early as 2011, Retrieved from the Internet on Feb. 16, 2015 at <URL: http://www.dsm.com/markets/anh/en_US/products/products-eubiotics/products-eubiotics-vevovitall.html>.

Seiko-pH Health Promoter water, Three Steps to Improve intestinal health via drinking water, product information available from Seiko, believed to be published at least as early as 2011, Retrieved from the Internet on Feb. 16, 2015 at <URL: http://www.amcra.be/sites/default/files/Jaco%20Eisen%20Selko%20Feed%20Additives.pdf>.

Seiko-pH, product information available from Seiko, believed to be published at least as early as 2011, Retrieved from the Internet on Feb. 16, 2015 at <URL: http://www.selko.com/en/products/selko-ph/9129>.

FloraMax B-11, (Tech Sheet) product information available from Ivesco, believed to be published at least as early as 2011 (product available since 2004), Retrieved from the Internet on Feb. 16, 2015 at <URL: http://www.ivescopoultry.com/Attachment/5/20535_5_FloraMaxTechSheet.pdf>.

FloraMax B-11 Proven in the lab . . . confirmed in the field, product information available from Pacific Vet Group, believed to be published at least as early as 2011 (product available since 2004), Retrieved from the Internet on Feb. 16, 2015 at <URL: http://www.pacificvetgroup.com/docs/PVG-FloraMaxB-11.pdf>.

Fortify Liquid Concentrated Direct-Fed Microbial for Drinking Water, product label available from Assist Natural Products and Services, LLC, believed to be published at least as early as 2013, Retrieved from the Internet on Feb. 16, 2015 at <URL: http://www.assist-nps.com/files/Fortify%20Liquid%20Label.pdf>.

Fortify Liquid, MSDS information available from Assist Natural Products and Services, LLC, believed to be published at least as early as 2013, Retrieved from the Internet on Feb. 16, 2015 at <URL: http://www.assist-nps.com/files/Fortify%20Liquid%20MSDS.pdf>.

Kem San Brand Liquid Antimicrobial, product specification available from Kemin Vet Innovations, Inc., 2100 Maury Street, Des Moines, Iowa 50317, published 2011.

Optimizer Proven in the lab . . . confirmed in the field, product brochure available from Pacific Vet Group-USA, Inc., 2135 Creek View Drive, Fayetteville, Arkansas 72704, published 2011.

Calsporin, product information available from Calpis Co., Ltd., 4-1, Ebisu-Minami 2-chome Shibuya, Tokyo, Japan, believed to be published at least as early as 2013 (product available since at least 2000).

Calsporin Swine FAQ, product information available from Quality Technology International, Inc., published 2012, Retrieved from the Internet on Feb. 16, 2015 at <URL: http://www.qtitechnology.com/sites/default/files/pdfs/CalsporinSwineFAQ.pdf>.

Calsporin Poultry FAQ, product information available from Quality Technology International, Inc., published 2012, Retrieved from the Internet on Feb. 16, 2015 at <URL: http://www.qtitechnology.com/sites/default/files/pdfs/CalsporinPoultryFAQ.pdf>.

Proflora Live DFM: Bacillus Subtilis Strain QST 713, product information available from Zoetis, 100 Campus Drive, Florham Park, New Jersey 07932, believed to be published at least as early as 2013.

Proflora Live DFM: Bacillus Subtilis Strain QST 713, product information available from Zoetis, believed to be published at least as early as 2013, Retrieved from the Internet on Feb. 16, 2015 at <URL: https://www.zoetisus.com/products/poultry/proflora.aspx>.

BioGrow & Provita Gameguard, product information available from Provita Eurotech Limited, 21 Bankmore Road, Omagh, County Tyrone, Northern Ireland, believed to be published at least as early as 2013 (BioGrow product available since 2001).

BioGrow, product information available from Provita, believed to be published at least as early as 2013 (BioGrow product available since 2001), Retrieved from the Internet on Feb. 16, 2015 at <URL: http://www.provita.co.uk/poultry/biogrow>.

Swine Bluelite 2Bw a water soluble acidified electrolyte product with probiotics for pigs, product information available from TechMix Global, published Sep. 2011, Retrieved from the Internet on Feb. 16, 2015 at <URL: https://web.archive.org/web/20110909124607/http://www.techmixglobal.com/swine-bluelite-2bw>.

Swine Bluelite 2Bw a water soluble acidified electrolyte product with probiotics for pigs, product information available from TechMix Global, believed to published at least as early as 2013 (product available since 2011), Retrieved from the Internet on Feb. 16, 2015 at <URL: https://www.techmixglobal.com/swine-bluelite-2bw>.

Swine Bluelite 2Bw a water soluble acidified electrolyte product with probiotics for pigs, product information available from TechMix Global, 740 Bowman St. , Stewart, MN, believed to published at least as early as 2013 (product available since 2011).

Timmermann et al., Metabolism and Nutrition Mortality and Growth Performance of Broilers Given Drinking Water Supplemented with Chicken-Specific Probiotics, Poultry Science, vol. 85, Aug. 1, 2006, pp. 1383-1388.

Katsutoshi et al., Effect of spore-bearing lactic acid-forming bacteria (Bacillus coagulans SANK 70258) administration on the intestinal environment, defecation frequency, fecal characteristics and dermal characteristics in humans and rats, Microbial Ecology in Health & Dis, Co-Action Publishing, SE, vol. 14, No. 1, Mar. 2002, pp 4-13.

\* cited by examiner

DELIVERY SYSTEM AND PROBIOTIC COMPOSITION FOR ANIMALS AND PLANTS

CROSS-REFERENCE TO RELATED APPLICATION

This application claims the benefit of U.S. Provisional Application Ser. No. 61/895,775 filed on Oct. 25, 2013.

BACKGROUND OF THE INVENTION

1. Field of the Invention

This invention relates to stabilized probiotic compositions, including synbiotic compositions and compositions used in conjunction with acidified drinking water, and a system and method for delivering the compositions to animals and plants.

2. Description of Related Art

Probiotics have been used in farm and agricultural applications for many years. A primary use for probiotic formulations is as a feed additive, but other uses include the treatment of housing, animal wound care, pond treatments, and water treatment. When used as a feed additive, the probiotic material is typically added directly to the feed (known as direct-fed microbials or "DFM") and consumed by the animal. DFM products are commercially available in a variety of product forms, including powder, paste, gel, bolus, and capsules, which may be mixed in feed, top-dressed, given as a paste, or mixed into drinking water or a milk replacer. Usage doses vary by product, from single dose applications to continuous feeding application. Most DFM products must be stored in a cool, dry area away from heat, direct sunlight, and high levels of humidity to avoid damaging the bacteria or rendering the bacteria ineffective as a probiotic. Some forms of commercially available DFM products contain bacterial spores, particularly *Bacillus* species, which are considered more stable and may have long shelf lives even under harsh environmental conditions, such as elevated temperatures, dryness and pH extremes. These spores will germinate into vegetative cells and grow when conditions become favorable. Several *Bacillus* species are approved by the Food & Drug Administration and the Association of American Feed Control Officials (AAFCO) for use in DFM products in the U.S., including *B. subtilis, B. licheniformis, B. pumilus, B. coagulans,* and *B. lentus*. Other countries have approved use of other *Bacillus* species as probiotic microorganisms.

Even relatively stable bacterial species used in DFM products may be sensitive to certain conditions typically found in application of DFM products to livestock. For example, the water activity in the feed can reduce the shelf-life of even the most stable bacterial forms. Various techniques are known to help increase shelf life of the bacteria in DFM products. Microencapsulation is one known method to increase shelf life of probiotic formulas to allow use in DFM products. For example, U.S. Pat. No. 6,254,910 discloses a delivery system for delivering unstable or sensitive ingredients, wherein the unstable or sensitive ingredient is coextruded with other food ingredients so that it is encapsulated within an outer layer of food ingredients, with each layer having specific moisture contents. Several probiotic species, including *Bacillus coagulans*, preferably in spore form, are disclosed in the '910 patent as unstable or sensitive ingredients that are suitable for encapsulation to protect the probiotic and increase the probability of survival during processing and in the environmental conditions of use. Other encapsulation technologies including spray drying extrusion, emulsion and phase separation have been used, but with limited success and added expense. A known encapsulated probiotic product, known as Bac-In-A-Box, is commercially available from SG Austria (http://www.sqaustria.com/probiotics). Newer microencapsulation techniques using calcium-alginate gel capsule formation appear promising, but are still in the development stage and are not yet suitable for large industrial applications.

Similarly, U.S. Pat. No. 5,501,857 discloses a capsule within a capsule having bacterial species, such as one from the genera *Lactobacillus* or *Bifidobacterium*, in the inner capsule and other beneficial ingredients, such as vitamins, in the outer capsule, with each capsule being surrounded by a gelatin shell. The capsule within a capsule structure allows the use of multiple beneficial ingredients that are not compatible within a single capsule. These capsules have the drawback of requiring direct oral administration to the animals. Similar direct oral administration compositions and methods are disclosed in WO 2010/079104, WO 2012/167882, and U.S. Patent Application Publication No. 2013/0017174. However, these formulas are generally complex and must be administered directly to each animal, which is time consuming and may be difficult.

It is also known to add probiotic bacteria to animal drinking water using a biogenerator to produce the bacteria in a vegetative state. Such a method is disclosed in U.S. Pat. No. 4,910,024, which describes a biogenerator technology and method for delivering temperature-sensitive probiotic bacteria in a live, vegetative condition into a potentially large number of domestic animals as a means of increasing nutrient absorption efficiency and controlling the proliferation of harmful microorganisms in the digestive tracts of such animals. There are several drawbacks to the use of an on-site biogenerator to deliver probiotics. A primary drawback is the difficulty with maintaining sterility or preventing contamination from external sources of bacteria, yeast, and fungi. Ideally, the water used in the biogenerator must be pathogen free and the device must prevent airborne transmission of undesirable microorganisms, which may grow in the device and be administered to the animals. These devices also require power and sufficient water pressure. Additionally, the growth of bacteria in the biogenerator is temperature dependent and the device would need to be temperature controlled to ensure proper growth of the bacteria. The normal ambient temperature and environmental variations (such as humidity) at sites where the device would typically be used, such as a barn, would result in adverse growth variations and inconsistencies without temperature and environmental control. DFM products that deliver vegetative state bacteria to the animals' feed or drinking water might also be more susceptible to the harsh stomach environment once ingested by the animals and may not survive to reach the intestinal tract where the probiotics are generally most effective. Additionally, the quantity of bacteria must be fed to the animals at the appropriate time and in a proper concentration to be effective, and this can be difficult to achieve with existing probiotic delivery technology.

There are also known systems for delivery of sterile liquids. For example, U.S. Pat. No. 5,320,256 discloses a system for delivering a sterile liquid comprising a compressible reservoir for storing the sterile liquid, a flexible delivery element extending from the reservoir with the delivery element having a hollow interior, and a series of shut off valves to allow delivery and prevent backflow of the liquid or air into the system. The '256 patent is not specifically related to delivery of probiotic formulas or delivery of sterile liquids to animals or in agricultural settings. Another example, which is specifically for delivery of medicines, vitamins, nutrients, and the like to animals, is found in U.S. Pat. No. 6,723,076. The delivery system disclosed in the '076 patent comprises a sealed, collapsible bag with two flexible tubes attached for filling the bag and administering the solution from the bag to an animal with a syringe gun. Although these systems address some of the problems associated with probiotic delivery, they do not address problems related to the environmental stability of the probiotic composition or automated and controlled dosing of the probiotic composition to a feed or water supply.

It is also known to administer probiotics to animals in spore form. In addition to the '910 patent discussed above, U.S. Pat. No. 4,999,193 discloses adding spores of bacteria, particularly *Bacillus cereus* (IP 5832 strain), to animal feed or drinking water. Spores are known to be able to withstand high temperatures, making them better suited for incorporation into animal feed during manufacture of the feed, which typically involves heat. Although the use of spore form bacteria addresses the problems associated with temperature stability, the prior art does not provide an adequate delivery system that eliminates outside contamination while achieving controlled delivery in a manner that is easily used in existing facilities without requiring any retrofitting or additional power sources.

In addition to providing probiotics, it also known to provide prebiotics in combination with probiotics. This combination is generally known as synbiotics. For example, WO 2012/027214 discloses a synbiotic combination of spore form *Bacillus* bacteria with prebiotic carbohydrates, including arabinoxylan, arabinoxylan oligosaccharides, xylose, soluble fiber dextrin, soluble corn fiber, and polydextrose. A prebiotic is a non-digestible carbohydrate or soluble fiber that provides a beneficial physiological effect on the host by selectively stimulating the favorable growth or activity of gut beneficial bacteria and/or reducing pathogenic populations. Prebiotics are resistant to digestive gastric acid and digestive enzymes in the animal's stomach and small intestine and are able to reach the large intestine substantially intact or only partially degraded (other than dissolving in water present in the gastrointestinal tract). Once in the large intestine, the prebiotics provide a carbohydrate food source for beneficial bacteria and undergo complete or partial fermentation in the colon (part of the large intestine within which additional nutrient absorption occurs through the process of fermentation). Fermentation occurs by the action of bacteria within the colon on the prebiotic food mass, producing gases and short-chain fatty acids (SCFA). The production of SCFAs, such as butyric acid, acetic acid, propionic acid, and valeric acids, is increased when prebiotics are added to animal feed. Scientific studies have indicated that SCFAs have significant health benefits. By increasing beneficial bacterial populations, prebiotics also suppress the populations of pathogenic bacteria in the colon, such as *Clostridia, E. Coli*, and *Salmonella*.

A variety of prebiotics are known, including polysaccharides, oligosaccharides, fructooligosaccharides (FOS), galactooligosaccharides (GOS), soya-oligosaccharides (SOS), xylo-oligosaccharides (XOS), pyrodextrins, isomalto-oligosaccharides (IMO), and lactulose. Specific water-soluble dietary fiber prebiotics also include Fructans (inulin), Xanthan Gum (E415), Pectin (E440), Natriumalginat (E401), Kaliumalginat (E402), Ammoniumalginat (E403), Calciumalginat (E404), PGA (E405), Agar (E406), and Carrageen (E407). Ingestion of these prebiotic fibers can change how other nutrients and chemicals are absorbed through bulking and viscositys and can also change the nature of the contents of the gastrointestinal tract, having been shown to increase populations of Lactobacilli and Bifidobacteria in the intestine and cecum of livestock. In poultry studies (particularly studies regarding broilers), providing a synbiotic combination of probiotic and prebiotic has been shown to increase the villus/crypt ratio (or ratio of villus height:crypt depth). The villus/crypt ratio is an indicator of the likely digestive capacity of the small intestine. It is within the small intestine that the final stages of enzymatic digestion occur, liberating small molecules capable of being absorbed, such as, sugars, monosaccharides, disaccharides, amino acids, dipeptides, and lipids. All of this absorption and much of the enzymatic digestion takes place on the surface of small intestinal epithelial cells, and to accommodate these processes, a huge mucosal surface area is required. The villi are minute (finger-like, hair-like, worm-like) projections from epithelial lining of the small intestine. Villus height is measured from the tip (top) of the villus to the villus-crypt junction. The villi are filled with blood vessels where the circulating blood takes picks up the nutrients. The crypt is the area between villi. Crypt depth is defined as the depth of the invagination, or in folding of the wall, between adjacent villi. Measurements for crypt depth are measured from the base upwards to the region of transition between the crypt and villus. Villus surface area is calculated by using formula, VW/2 times VL, where VW equals the villous width and VL equals villus length. More surface area provides more absorption of nutrients. The increase in villus/crypt ratio found in the poultry symbiotic study indicates an increase in digestion and absorption of nutrients.

Some studies have also shown the importance and benefits of this kind of synergy between probiotics and prebiotics and the effectiveness in helping young animals to achieve better growth performance. Studies using *B. subtilis* as the probiotic and inulin as the prebiotic have shown that the combination is more effective in swine and poultry populations than the use of *B. subtilis* alone. For example, this synbiotic combination was shown to reduce (P<0.05) excreta pH, intestinal digesta and cecal content pH compared with a control group. The combination also modulated the ileal and caecal microflora composition by decreasing (P<0.05) numbers of *Clostridium* and Coliforms and increasing (P<0.05) numbers of Bifidobacteria and Lactobacilli compared with a control group. In another study, weaned piglets were shown to have increased levels of butyrate (a SOFA) when fed with a diet containing prebiotics. The importance of butyrate on gut improvement is well known, as this is crucial to optimize nutrient absorption.

Another issue encountered in animal and plant watering systems is bacteria populations in the drinking water and water transport systems. Municipal water supplies typically have some levels of bacteria present and local sources of water (such as an on-site pond) may contain bacteria from surrounding soil, fish, and run-off. These bacteria are known to result in or contribute to the formation of biofilms in the drinking water system. Biofilms are formed when microbial cells attach to surfaces in the water system, such as pipes and drinking nipples/nozzles, and form a film or slime layer. These biofilms can build-up, resulting in clogging parts of the system, or portions of the biofilm may also break-off causing additional clogging in other areas of the system, which reduce the amount of water available to the animals or plants. One known method for removing biofilms in these water systems is to flush the film by increasing the pressure in the water line. This method may cause damage to parts of the water system and typically leaves behind a mineral deposit from the biofilm, which will serve as a shelter for micro-organisms and result in the biofilm being reestablished. Chemical treatment products, such as chlorine and hydrogen peroxide are also known to be used and have good sanitizing abilities; however, these products are not beneficial to gut health for the animals or soil health for plants and may even be harmful.

It is also know to acidify the water by adding certain organic acids to the water. The use of acidified water is beneficial for several reasons, including that the acid, in its non-dissociated form, can penetrate through the bacterial wall and destroy certain microorganisms, which can reduce biofilm formation in the water system, aid in keeping drinking trough, nipples/nozzles clean, and can reduce the number of bacteria in the water. Since the bacteria in the water may be pathogenic and may cause illness when ingested by the animal, reduction of the bacteria in the water may be particularly helpful in light of bans on antibiotic use in certain geographic areas, such as Europe. Additionally, when ingested by animals in sufficient quantities to result in a stomach pH below about 6, the growth of pathogenic microorganisms (from other sources, such as food) is inhibited. Typically, weak organic acids, such as acetic acid, butyric acid, lactic acid, and sorbic acid, are used to acidify drinking water. There are a number of drawbacks to or difficulties with acidifying drinking water. For example, it can be difficult to maintain the pH level at a desired range (below 7 and usually below 5.5). Applying single acids in drinking water typically results in the pH decreasing quickly, which can have negative results, such as less water intake and decreased performance, including lower feed conversion rate and lower daily weight gain in the animals. For example, during a period of disease, pigs will drop their feed intake but maintain their water intake. Thus, palatable water is important for the GIT health of the animals. The use of acids can also be corrosive to metal components in the water system, resulting in added repair and replacement costs. To decrease these effects, a mix of organic acids may be used to acidify the drinking water, since the mix has a buffering effect that makes the pH decrease slowly. A synergistic mix of organic acids has also a greater antibacterial effect, is more tasteful, and is less corrosive when compared with single acids. Incorrect use of acidified drinking water can also result in proliferation of bacterial populations and growth of algae (which can result in further clogging of the water system) and reduction of feed intake (which can result in decreased weight gain and inadequate absorption of nutrients). Additionally, some acids are known to cause fungal growth, which can clog system parts and be detrimental to the animal.

Although it is known to use probiotics alone or in combination with prebiotics and to separately use acidified drinking water to provide health benefits to animals and to improve cleanliness in plant and animal water systems, it has not previously been known to combine probiotics, prebiotics, and acidified drinking water together to provide synergistic health benefits.

SUMMARY OF THE INVENTION

This invention relates to stabilized probiotic compositions, including compositions comprising probiotics and prebiotics, and a system and method for delivering the compositions to animals and plants, including delivering the compositions with acidified water to provide additional benefits. The probiotic compositions comprise suspended probiotic spores that are stable over a wide range of environmental conditions, including temperature fluctuations that would typically be encountered in farm and agricultural settings. The compositions are thermally stable and will not settle, change composition or activity under the extreme conditions found in these animal farming and similar settings. The preferred probiotic compositions according to the invention comprise one or more species from the $Bacillus$ genus in spore form, which are stable during adverse conditions.

According to one preferred embodiment, the composition comprises bacteria spores, about 0.00005 to 3.0% by weight surfactant, about 0.002 to 5.0% by weight thickener, and optionally about 0.01 to 2.0% by weight of acidifiers, acids, or salts of acids (including those used as a preservative or stabilizer), with the balance being water. According to another preferred embodiment, the composition comprises bacterial spores, about 0.1 to 5.0% by weight thickener, about 0.05 to 0.5% by weight acids or salts of acids, optionally about 0.1-20% by weight water activity reducers, and optionally about 0.1% to 20% additional acidifier (acids or salts of acids), with the balance being water. The optional acidifiers reduce the pH of the composition to beneficial levels and may be used to acidify smaller quantities of drinking water when the composition is added to drinking water according to a preferred method of use, as discussed in more detail below.

Most preferably, the bacterial spores in both preferred embodiments are in a dry, powder blend of 40-60% salt (table salt) and 60-40% bacteria spores that combined make up about 0.1 to 10% by weight of the composition. The compositions preferably comprise around $1.0 \times 10^8$ to around $3.0 \times 10^8$ cfu/ml of the composition (spore suspension), which when diluted with drinking water (for animal watering applications) provide around $10^4$ to $10^6$ cfu/ml bacterial strains in the drinking water. Most preferably, the thickener in both preferred embodiments is one that also acts as a prebiotic, such as xanthan gum, to provide additional benefits.

The system and method for delivering probiotic compositions, and preferably those compositions according to the invention and including prebiotics, or other treatment compositions or sterile liquids comprises packaging the compositions or liquids in a container and delivering them directly to a planter or a water or feed station using gravity feed or a battery powered non-contact pump. The compositions or liquids are preferably packaged in a container, most preferably a collapsible pouch or bag with an attached or attachable tube (similar to an IV-bag or a Mylar bag with an integrated dispensing port attachable to tubing). Depending on the type of container used, the container and tubing may be sterilized or may be used without sterilization. By using the systems of the invention, the probiotic composition is protected from contamination by other, outside bacterial species or fungi or the like, while it is being stored at the site of consumption prior to being dispensed to the animal or plant. The composition or liquid is delivered from the container through the delivery tube to animal feed stations, animal water supply troughs, pressurized drinking water lines, ponds, planters, and the like. The delivery through the tube is controlled by a non-contact pump or gravity feed with a valve to control the flow of the composition. The pump or valve are controlled so that the flow of the composition can be selectively started and stopped for certain durations as needed to achieve a proper dosage or volume of discharge, depending on the particular composition or liquid involved and the animal or plant species to which the composition or liquid are being delivered, or to time the dosage to match a particular feeding and drinking schedule. The pump or valve may also be controlled in response to external stimuli, such as motion or light. It is not necessary to vent the collapsible bag, so airborne contaminates and undesirable bacteria are not introduced into the feed container. According to one preferred embodiment, a duck-bill type valve or similar mechanism is attached to the end of the delivery tube to prevent any contaminants or undesirable bacteria from growing in the end of the tube. Whether used with a non-contact pump or gravity feed, the feed container is preferably hung at a sufficient height above the pump or discharge point to provide sufficient hydrostatic pressure to feed the pump or discharge the composition, and to protect it from the animals. To aid in securing the container and protecting it from possible puncturing, it may optionally be placed or hung inside a protective cabinet or housing. The system and method for delivering compositions and liquids according to the invention is simple and low-cost and does not require an on-site source of sterile water or electric power supply to operate.

BRIEF DESCRIPTION OF THE DRAWINGS

The system and method of the invention are further described and explained in relation to the following drawings wherein.

DESCRIPTION OF THE PREFERRED EMBODIMENTS

Figure 2:
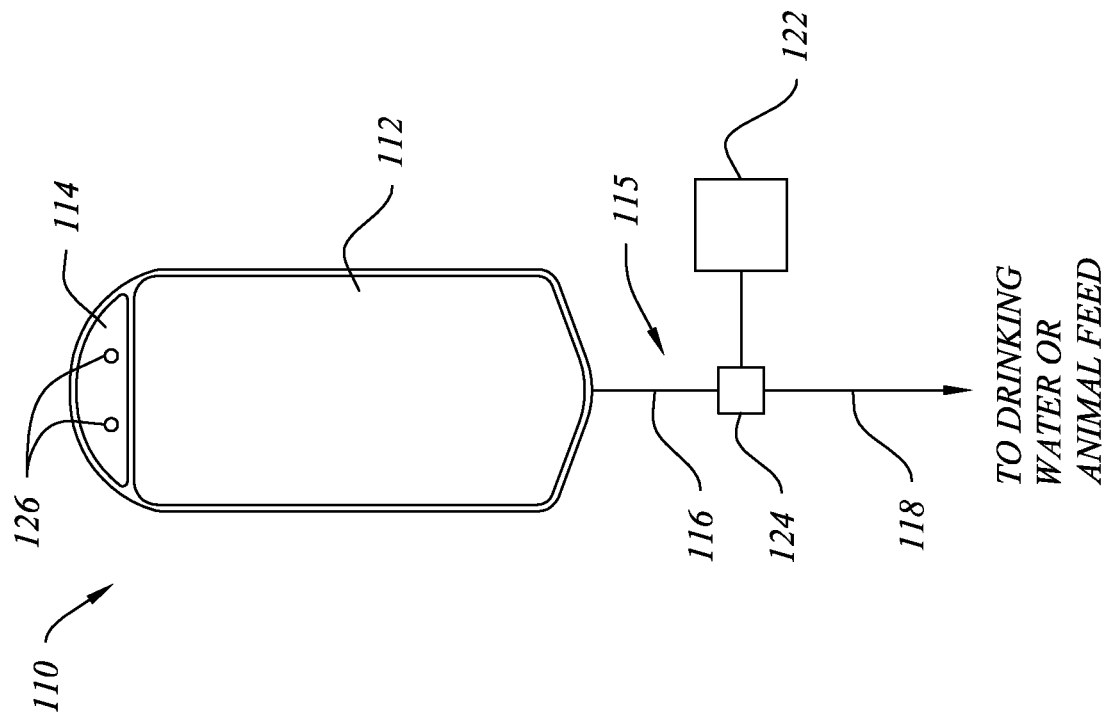
FIG. 2 is a side elevation view of another embodiment of a delivery system according to the invention.
Figure 1:
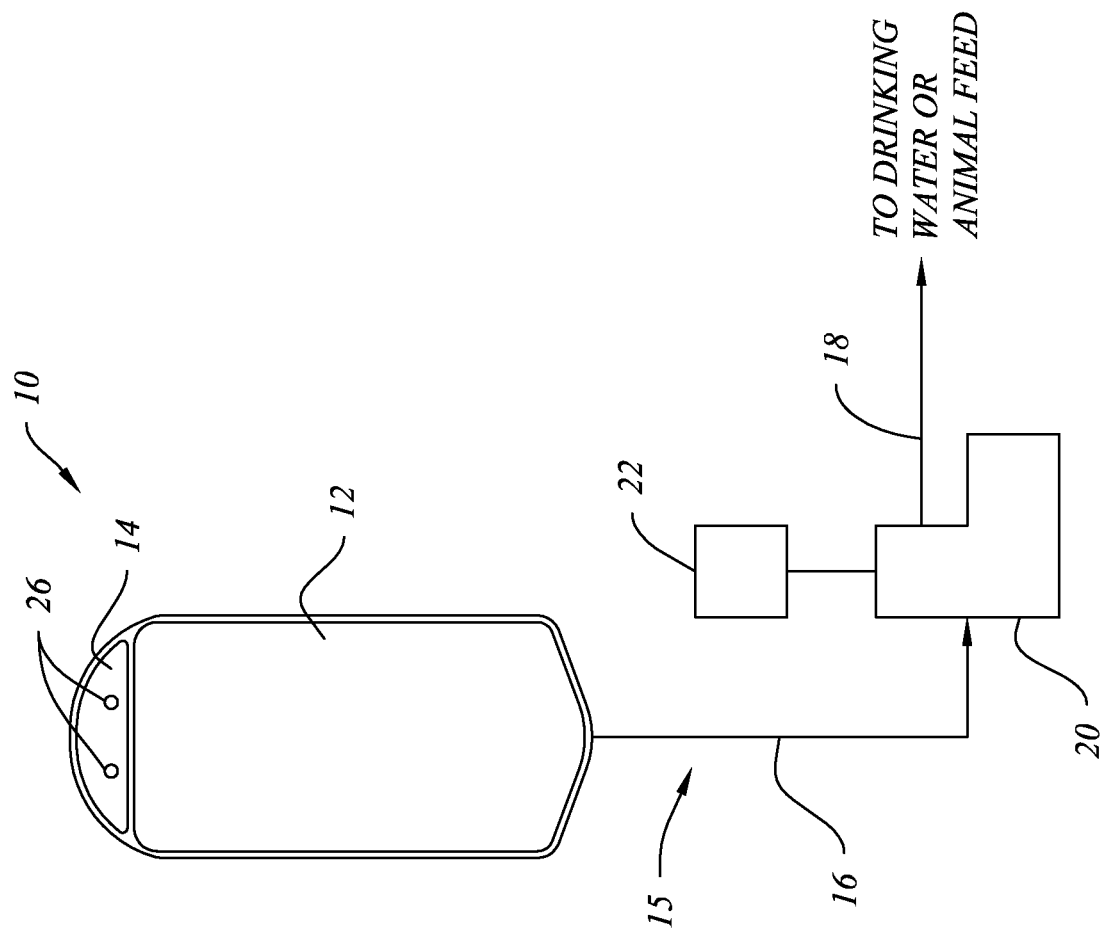
FIG. 1 is a side elevation view of one embodiment of a delivery system according to the invention.

A probiotic composition according to one preferred embodiment of the invention comprises one or more bacterial species, a surfactant, and a thickener, and optionally one or more acidifiers, acids or salts or acids to act as a preservative. A probiotic composition according to another preferred embodiment of the invention comprises one or more bacterial species, a thickener, one or more acidifiers, acids or salts of acids, and optionally a surfactant. Either embodiment may also optionally include prebiotics, to the extent the thickener is not also a prebiotic or in addition to any thickener that is a prebiotic. Either embodiment may also optionally include one or more water activity reducers. Most preferably, the compositions according to the invention comprise various species of suspended probiotic spores, as described in more detail below. The use of these species in spore form increases the stability of the probiotics in the harsh environmental conditions, particularly temperature fluctuations that occur in stables, barns, and other farm and agricultural settings.

A suitable thickener is included in the composition according to both preferred embodiments. The thickener is preferably one that does not separate or degrade at varying temperatures typically found in non-climate controlled environments, such as barns, farms, and nurseries. The thickener aids in stabilizing the suspension so the bacterial mixture remains homogenous and dispersed through a volume of the composition and does not settle out of the suspension. When used with the system and method of delivery described below, this ensures that the concentration of probiotic materials is evenly distributed throughout the container so that the dosage of probiotic material delivered remains consistent or relatively consistent (depending on the specific delivery method and control mechanism used) throughout a treatment cycle.

The most preferred thickener in either embodiment is xanthan gum, which is a polysaccharide composed of pentasaccharide repeat units of glucose, mannose, and glurcuronic acid and a known prebiotic. Unlike some other gums, xanthan gum is very stable under a wide range of temperatures and pH. Xanthan gum, like all soluble fibers, helps balance intestinal pH and tends to slow the movement of food and extends the mouth to cecum transition time. This slowing may allow more time for the spores to germinate in the stomach before reaching the intestines, which allows for use of the more stable spore form bacteria rather than the use of vegetative bacteria that may not survive the harsh environmental conditions of use or may not survive the animal's stomach. Another preferred thickener is acacia gum, which is also a known prebiotic. Other preferred thickeners include locust bean gum, guar gum and gum arabic, which are also believed to be prebiotics. In addition to prebiotic benefits, these fibers do not bind to minerals and vitamins, and therefore, do not restrict or interfere with their absorption and may even improve absorption of certain minerals, such as calcium. Other thickeners that are not considered prebiotics may also be used.

Either embodiment may optionally include one or more prebiotics, which are preferably used if the thickener used is not a prebiotic but may also be used in addition to a prebiotic thickener. Prebiotics are classified as disaccharides, oligosaccharides and polysaccharides, and can include Inulin, Oligofructose, Fructo-oligosaccharides (FOS), Galacto-oligosaccharide (GOS), trans-Glacto-Oligosaccharides (TOS) and Short-Chain Fructo-oligosaccharides (scFOS), soy Fructo-oligosaccharide (soyFOS), Gluco-oligosaccharides, Glyco-oligosaccharides, Lactitol, Malto-oligosaccharides, Xylo-oligosaccharides, Stachyose, Lactulose, Raffinose. Mannan-oligosaccharide (MOS) are prebiotics may not enrich probiotic bacterial populations, but will bind with and remove pathogens from the intestinal tract and are believed to stimulate the immune system.

Both embodiments preferably include one or more acidifiers, acids, or salts of acids to act as a preservative or to acidify the composition. Preferred preservatives are acetic acid, citric acid, fumaric acid, propionic acid, sodium propionate, calcium propionate, formic acid, sodium formate, benzoic acid, sodium benzoate, sorbic acid, potassium sorbate, and calcium sorbate. Other known preservatives, preferably generally regarded as safe (GRAS) food preservatives, may also be used. One or more of these same acids or salts or acids may also be optionally added as an acidifier, in addition to any amount used as a preservative. Depending on the dosing mechanism and environment, the optional acidifier may be used to acidify a smaller amount of drinking water, such as the water at a single, smaller scale trough. For larger water systems and multiple troughs or drinking stations, it is preferred to use a separate acidification system since larger quantities of acid or salts or acids will be need to reduce the pH of the larger volume of water. Even if not used to fully acidify the drinking water, these acids and salts of acids aid in reducing the pH of the composition. Preferably, the pH of the composition is between about 4.0 and 7.0. More preferably it is between about 4.0 and 5.5 and most preferably around 4.5. Reducing the pH of the composition may have antimicrobial activity with respect to yeast, molds, and pathogenic bacteria.

One or more water activity reducers, such as sodium chloride, potassium chloride, or corn syrup (a 70% solution of corn syrup), are optionally included in the composition according either preferred embodiment. The water activity reducer aids in inhibiting microorganism growth, so that the bacterial spores do not prematurely germinate while the composition is being stored prior to the time it is discharged to the point of consumption by the animals or plants to be treated. They also aid in inhibiting growth of contamination microorganisms The first embodiment preferably includes a surfactant, but it is optional in the second embodiment. The surfactant is preferably one that is safe for ingestion by animals, although other surfactants may be used with other applications, such as delivery to plants. Most preferably, the surfactant is Polysorbate 80. Although any GRAS or AAFCO approved surfactants or emulsifiers may be used with either embodiment, there are concerns that some animals may not tolerate all approved surfactants well. Because the benefits of the surfactant in stabilizing the suspension so the bacterial mixture remains homogenous and does not settle out may also be achieved by the use of the thickener, it is not necessary to add the surfactant. If a surfactant is used in the composition according to this second embodiment, it is preferably used in about the same weight percentage range as in the first embodiment.

Most preferably, the bacterial species used in both embodiments are one or more species from the *Bacillus* genus. The most preferred species for the probiotic bacteria include the following: *Bacillus pumilus, Bacillus licheniformis, Bacillus amylophilus, Bacillus subtilis, Bacillus amyloliquefaciens, Bacillus clausii, Bacillus firmus, Bacillus megaterium, Bacillus mesentericus, Bacillus subtilis* var. *natto,* or *Bacillus toyonensis*, but any *Bacillus* species approved as a probiotic in the country of use may also be used. It is preferred that the bacteria are in spore form, as the spore form is more stable to environmental fluctuations, such as ambient temperature changes. Additionally, as compared to vegetative state DFM, spores are believed to be better able to survive through the stomach once ingested by an animal to germinate in the intestines, where they are beneficial. Most preferably, the spores used in the compositions according to the invention are a dry powder blend that comprises around 40-60% salt (table salt) and 60-40% bacterial spores. The spores are spray-dried from a liquid fermentation concentrate. Salt is used to dilute the pure spray-dried spore powder to a standard spore count in the final spore powder blend. During production fermentation, different *Bacillus* strains will grow at different rates, resulting in varying final count numbers for the fermentation batch liquor. The fermentation liquor is centrifuged to concentrate the spores in the liquor. Then, the concentrated liquor is spray-dried which results in a powder containing only *Bacillus* spores. The addition of salt to the spray-dried *Bacillus* spore powder aids in standardizing the spore blend count per gram from batch to batch. Other forms of bacterial spores or spore blends may also be used. Most preferably, the dry spore blend is pre-mixed with a portion of the water used in the composition, around 3-30% of the total water, and the resulting bacteria spore solution is added to the other ingredients, including the remaining water. This aids in dispersing the bacteria spores throughout the composition.

A probiotic composition according to a first preferred embodiment of the invention preferably comprises bacterial spores that provide $10^8$ cfu/ml of the spore suspension (most preferably around $1.0 \times 10^8$ to around $3.0 \times 10^8$ cfu/ml of composition, which, when diluted in drinking water provides approximately $10^4$ to $10^6$ cfu/ml drinking water), 0.00005 to 3.0% surfactant, and 0.002 to 5.0% thickener, and optionally the about 0.01 to 2.0% of one or more acids or salts of acids as a preservative. A probiotic composition according to a second preferred embodiment of the invention comprises bacterial spores that provide $10^8$ cfu/ml of the spore suspension (which, when diluted in drinking water provides approximately $10^4$ to $10^6$ cfu/ml drinking water), about 0.1 to 5.0% thickener (preferably one that also acts as a prebiotic), about 0.05-0.5% of one or more preservatives, optionally about 0.1-20% of one or more water activity reducers, and optionally 0.1-20% of one or more acidifiers. The balance of the composition in both preferred embodiments is water and the percentages herein are by weight. It is preferred to use deionized or distilled water, to remove salts or outside bacteria, but tap water or other sources of water may also be used.

Several examples of probiotic compositions according preferred embodiments of the invention were made and tested for different parameters. These compositions are set forth in Table 1 below.

TABLE 1

| Ingredient | Formula No. | | | | | | | |
|---|---|---|---|---|---|---|---|---|
| | 1 | 2 | 3 | 4 | 5 | 6 | 7 | 8 |
| Potassium Sorbate | 0.33% | 0.33% | 0.1% | 0.1% | 0.1% | 0.1% | 0.1% | 0.1% |
| Citric Acid | 0.34% | 0.34% | 0.1% | 0.1% | 5.0% | 0.1% | 0.1% | 0.1% |
| Sodium Benzoate | 0.33% | 0.33% | 0.1% | 0.1% | 0.1% | 0.1% | 0.1% | 0.1% |
| Benzoic Acid | — | — | — | 0.1% | — | 0.1% | 0.1% | — |
| Sorbic Acid | — | — | — | 0.1% | — | — | 0.1% | — |
| Sodium Propionate | — | — | — | — | 10.0% | 0.1% | — | — |
| Xanthan Gum | 0.2% | 0.2% | 0.2% | 0.3% | 0.4% | 0.4% | 0.5% | 0.5% |
| Sodium Chloride | 0.2% | 0.2% | — | 0.2% | — | 0.2% | 0.1% | 0.2% |
| Potassium Chloride | — | — | — | — | — | — | 0.1% | 0.1% |
| Spore Blend | 0.1% | 0.1% | 0.1% | 0.1% | 0.1% | 0.1% | 0.1% | 0.1% |

The balance of each composition is water (around 1 L in these samples). Deionized water was used in each composition, except composition No. 1, which used tap water. The percentages indicated are by weight. Each formula was targeted to have a pH between about 4.0 and 5.5, but some formulas were found to have actual pH values far less than expected. Formula No. 1 was targeted to have a pH between 5.0 and 5.5, but its actual pH was around 2.1-2.3, which is too low and may be harmful to the spores, create stability issues with packaging, and be subject to more restrictive transportation regulations. Formula No. 1 also exhibited weak thickening. Formula No. 2 is the same as No. 1, except the source of water is different. Formula No. 2 had an actual pH of around 2.2-2.3 and also exhibited weak thickening. The amount of acids and salts of acids in Formula No. 3 was decreased to raise the pH and to determine if the thickness improved while using the same amount of thickener as in Nos. 1 and 2. While Formula No. 3 was an improvement over Nos. 1 and 2, it still exhibited weak thickening and its actual pH was 6.6, over the target value range. Additional acids were added to Formula No. 4 to lower the pH and additional thickener was added. Formula No. 4 had improved thickening, but further improvements in thickening would be beneficial. The amount of acid in Formula No. 5 was substantially increased, which resulted in an actual pH of around 1.0. The amount of acid in Formula No. 6 was decreased and the thickener increased, which resulted in a composition that was too thick to drop. Formula No. 7 increased the thickener and amount of water activity reducers, but exhibited issues with mixing of benzoic acid and sorbic acid. The benzoic acid and sorbic acid were removed in Formula No. 8. Formula Nos. 1-7 provided $2\times10^{11}$ cfu/gm and No. 8 provided $1\times10^{11}$ cfu/gm bacteria spores. Of these sample formulas, No. 8 is the most preferred as it exhibited adequate thickening and had an actual pH of around 4.5+/−0.2, and used less spore blend.

It is preferred that the compositions according the embodiments of the invention use around 0.01% to around 0.3% bacteria spore blend and more preferably between about 0.03% to 0.1% bacteria spore blend. A reduction in the amount of spore blend used substantially reduces the costs of the composition. Depending on the end use application, differing amounts of spore blend may be used in the compositions according to the invention. For example, smaller percentages of spore blend may be used in the compositions for use with chickens, whereas larger percentages would be used in composition for use with pigs.

A composition according to formula No. 8 was tested for shelf-life at various temperatures. Samples of Formula No. 8 were sealed in a plastic bag, such as one used in a preferred delivery system as described below, and stored for two months at temperatures around 4-8° C. (39-46° F.), 30° C. (86° F.), and 35° C. (95° F.) to simulate typical temperature ranges in which the probiotic composition may be stored and used in agricultural settings. At the end of the first month of the storage period, each sample was observed and tested. All three samples had a pH of around 4.5 and there was no settling, layering or change of appearance in any of the three samples, indicating that the bacteria spores remained suspended and dispersed throughout the composition during the storage period. None of the samples contained any fungal contamination or gram-negative bacteria contamination. At time count zero (when the samples were initially stored), each sample contained bacteria spores of around $2.12\times10^{8}$ cfu/mL. At the end of the one month storage period, the samples contained bacteria spores of around $2.09\times10^{8}$ cfu/mL spore suspension (lowest temperature sample), $1.99\times10^{8}$ cfu/mL (middle temperature sample), and $2.15\times10^{8}$ cfu/mL (high temperature sample). The bacteria counts are somewhat variable in different samples, especially thickened samples; however, these are considered to be comparable counts. Each sample was tested again after two months in storage. The samples contained bacteria spores of around $2.08\times10^{8}$ cfu/ml (lowest temperature sample); $2.01\times10^{8}$ cfu/ml (middle temperature sample); and $2.0\times10^{8}$ cfu/ml (high temperature sample). The target shelf life is around $2\times10^{8}$ cfu/ml spore suspension, so the samples are within the targeted shelf life after two months of storage. These test results demonstrate that probiotic compositions according to a preferred embodiment of the invention are stable over a range of temperatures, with the bacteria spores remaining viable, suspended, and dispersed throughout the composition. The spore blend (40-60% spore powder and 60-40% salt) used in each sample formula was the same, providing at least around $2\times10^{11}$ spores/gram. The spore species in the blend were multiple *Bacillus subtilis* and *Bacillus licheniformis* strains. The spore blend powder was premixed with 100 mL of water with stirring for 30 minutes prior to adding to the other ingredients. Premixing with water aids in mixing the spore blend with the other ingredients and dispersing the spores throughout the composition.

Another aspect of the invention is a system and method for delivering probiotic compositions, and preferably probiotic compositions according to the invention as described herein, directly into animal feed or drinking water at the point of consumption. Although it is preferred to use probiotic compositions comprising one or more *Bacillus* species as according to the compositions of the invention, the system of the invention may be used with compositions comprising other bacteria genera and other species. For example, one or more species from the following genera: *Bacillus, Bacteroides, Bifidobacterium, Pediococcus, Enterococcus, Lactobacillus*, and *Propionibacterium* (including *Bacillus pumilus, Bacillus licheniformis, Bacillus amylophilus, Bacillus subtilis, Bacillus amyloliquefaciens, Bacillus clausii, Bacillus firmus, Bacillus megaterium, Bacillus mesentericus, Bacillus subtilis* var. *natto*, or *Bacillus toyonensis Bacteroides ruminocola, Bacteroides ruminocola, Bacteriodes suis, Bifidobacterium adolescentis, Bifidobacterium animalis, Bifidobacterium bifidum, Bifidobacterium infantis, Bifidobacterium longum, Bifidobacterium thermophilum, Pediococcus acidilacticii, Pediococcus cerevisiae, Pediococcus pentosaceus, Enterococcus cremoris, Enterococcus diacetylactis, Enterococcus faecium, Enterococcus intermedius, Enterococcus lactis, Enterococcus thermophilus, Lactobacillus delbruekii, Lactobacillus fermentum, Lactobacillus helveticus, Lactobacillus lactis, Lactobacillus plantarum, Lactobacillus reuteri, Lactobacillus brevis, Lactobacillus buchneri, Lactobacillus bulgaricus, Lactobacillus casei, Lactobacillus farciminis, Lactobacillus cellobiosus, Lactobacillus curvatus, Propionibacterium acidipropionici, Propionibacterium freudenreichii, Propionibacterium shermanii*) and/or one or more of the following species: *Leuconostoc mesenteroides, Megasphaera elsdennii* may be used with the system and method of the invention.

Referring to FIG. 1, one preferred embodiment of a delivery system 10 is depicted. Delivery system 10 preferably comprises a container 12, tubing 15, non-contact pump 20, and controller 22. Container 12 is preferably a collapsible bag, similar to an IV bag, containing the probiotic composition. An upper end 14 of container 12 is preferably a sealed-off section of the collapsible bag through which one or more holes 26 are provided to facilitate hanging container 12 from hooks or a nail at the site of consumption. Alternatively, container 12 may be hung from clips or similar mechanisms and upper end 14 may include externally protruding ridges to aid in securing container 12 to such clips. Container 12 may be sterilized, preferably by UV sterilization, prior to container 12 being filled with a probiotic composition to ensure there is no contamination. Optionally, air may be removed from the head space in the container, but it is not necessary. Attached at or attachable to a lower end of container 12 is a tube 15 having a first portion 16 disposed near container 12 and a second portion 18 disposed near the point of consumption where the probiotic formula will be dispensed. Tube 15 may be integrally formed with container 12 or pre-attached to container 12, as will be understood by those of ordinary skill in the art, prior to shipping to the site of use. Tube 15 may also be sterilized, preferably by UV sterilization, prior to shipping. When integrally formed with or pre-attached to container 12, the distal end of tube portion 18 is preferably sealed with a removable seal or covering, or may include a valve, to seal-off container 12 once filled with a probiotic composition. The seal or covering would be removed or the valve opened when the probiotic composition is ready to be dispensed at the point of use.

Tube 15 passes through a non-contact pump 20, such as a peristaltic pump, which allows the probiotic composition to be pumped from container 12 through tubing 15 to be dispensed at the point of consumption without any potentially contaminating contact with the pump or the exterior environment in which system 10 is being used. Container 12 preferably collapses as it is emptied by the pumping action without the need for an air vent. Pump 20 is preferably battery operated so that an external power source is not needed, making it easy to add system 10 to existing animal feed or drinking locations, but may also be adapted to connect to an outlet or other external power source.

Container 12 is preferably hung above pump 20 at a sufficient height to provide the head pressure needed to deliver the probiotic composition to an inlet on pump 20. Most preferably, the lower end of container 12 will be hung at least 6 inches above the inlet to pump 20. The distal end of tube portion 18 preferably includes a "duck bill" valve or similar mechanism to prevent any contamination by backflow into the tubing. The distal end of tube portion 18 may also include spray or dispersion structures designed to dispense the probiotic composition in a wider pattern. A wider dispersion pattern is particularly preferred if the probiotic composition is dispensed into stagnant drinking water, a large water or feed trough, dry animal feed, or animal housing or bedding material in order to spread the composition over more surface area. A wider dispersion pattern may also avoid saturating dry feed with moisture. The distal end of tube portion 18 may also be split into multiple tubes or attached to a manifold to facilitate delivery of the probiotic composition to multiple locations, such as multiple drinking troughs within a barn.

A controller 22 is preferably connected to pump 20 to periodically activate the pumping action. Controller 22 may comprise one or more control mechanisms for activating pump 20, such as a simple timer that activates pump 20 for a given duration or cycle at specified time intervals. For example, controller 22 may be a timer programmed to activate pump 20 for a 60 second cycle every six hours. Other control mechanisms may also be used in addition to or in place of a timer. For example, a motion detector may be used in conjunction with a timer to activate pump 20 for a 60 second cycle when motion is detected for a specified period of time. Such a mechanism would allow the probiotic composition to be delivered to the animal's drinking water or feed when the presence of animals is detected by motion. This has the advantage over a timer only control mechanism, which may dispense the probiotic composition when no animals are present and may result in wasting the probiotic. The bacteria in the probiotic compositions according to the invention may survive for hours after being dispensed, so that they are likely to still be viable when an animal arrives to feed or drink even if it was dispensed when no animals are present, so dispensing when animals are present is not critical. The controller 22 may also be configured to sense ambient light conditions (such as daylight or simulated daylight, when animals are more likely to be eating or drinking) or temperatures, or other variables that may be encountered at the point of consumption. Sensing these conditions may result in the probiotic composition being dispensed at times when the animals are more likely to be active and feeding or drinking to avoid wasting the probiotic composition.

The controller 22 may also be configured to sense RFID tags, or similar technology, attached to the animals. The controller 22 would read the signal from the RFID tag, determine which animal is present, and selectively trigger the pump to dispense the probiotic composition if the animal is to receive the probiotics. This may be particularly useful if it is desired to provide probiotics to certain animals, but is not considered necessary for other animals, without requiring individual administration of a capsule or injection. The use of RFID tags may also allow the system to monitor how long an animal is present at the water or feeding station, which may be used to correlate how much probiotic was actually ingested. Other control mechanisms may be used with the invention, as will be understood by those of ordinary skill in the art. Controller 22 is preferably battery operated so that an external power source is not needed, making it easy to add system 10 to existing animal feed or drinking locations, but may also be adapted to connect to an outlet or other external power source. Controller 22 may be incorporated into pump 20 and need not be a separate component of system 10.

Referring to FIG. 2, a preferred embodiment of a delivery system 110 is depicted. Delivery system 110 relies on gravity to dispense the probiotic compositions, rather than a pumping system. Delivery system 110 preferably comprises a container 112, tubing 115, valve 124, and controller 122. Container 112 is preferably a collapsible bag, similar to container 12. Tubing 115 preferably comprises a first portion 116 disposed near container 112 and a second portion 118 disposed near the point of consumption where the probiotic composition will be dispensed. Rather than passing through a non-contact pump, as in system 10, a valve 124 is disposed along the length of tubing 115 (separating portion 116 from 118). The features previously described for container 12 and tubing 15 are also applicable to container 112 and tubing 115. Valve 124 is preferably a pinch valve, but other types of valves may also be used. Actuation of valve 124 from an open to closed position is controlled by controller 122. The various control mechanisms for controller 122 are the same as for controller 22. As the probiotic composition in container 112 is dispensed, the head pressure will change and the amount of probiotic dispensed will vary over time unless the controller 122 is programmed to keep the valve open longer or to open with greater frequency as the volume of probiotic composition within container 112 decreases. For simplicity, controller 122 may be programmed for the lowest expected head pressure. Variations in the programming may be set according to the height at which container 112 is hung. Most preferably, the lower end of container 112 will be hung at least 6 inches above the level of dispensing at the end of tubing portion 118. Controller 122 is preferably battery operated so that an external power source is not needed, making it easy to add system 110 to existing animal feed or drinking locations, but may also be adapted to connect to an outlet or other external power source.

Figure 3:
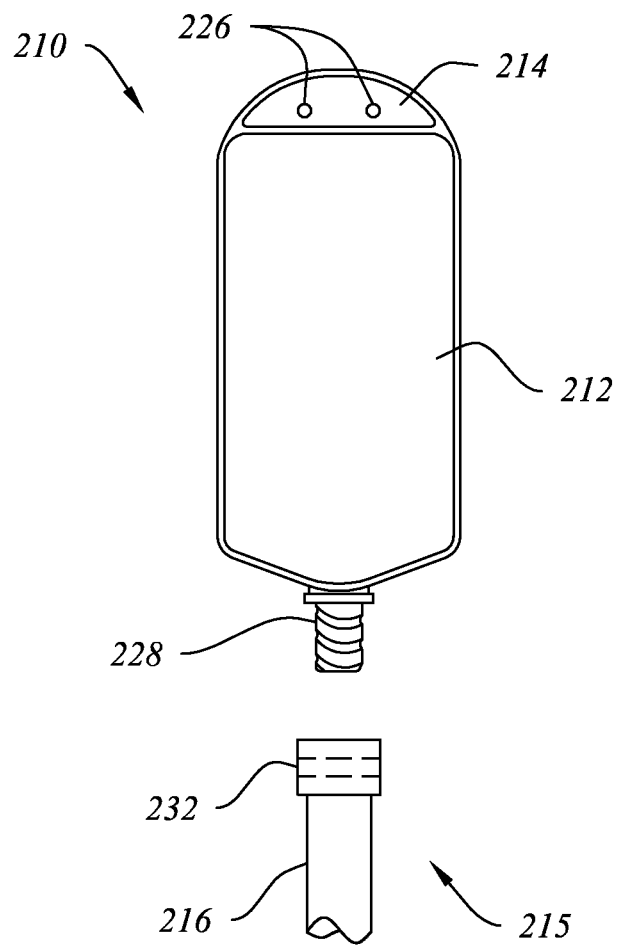
FIG. 3 is a side elevation view of an alternative container and tubing for use with the delivery systems according to the invention.
Figure 4:
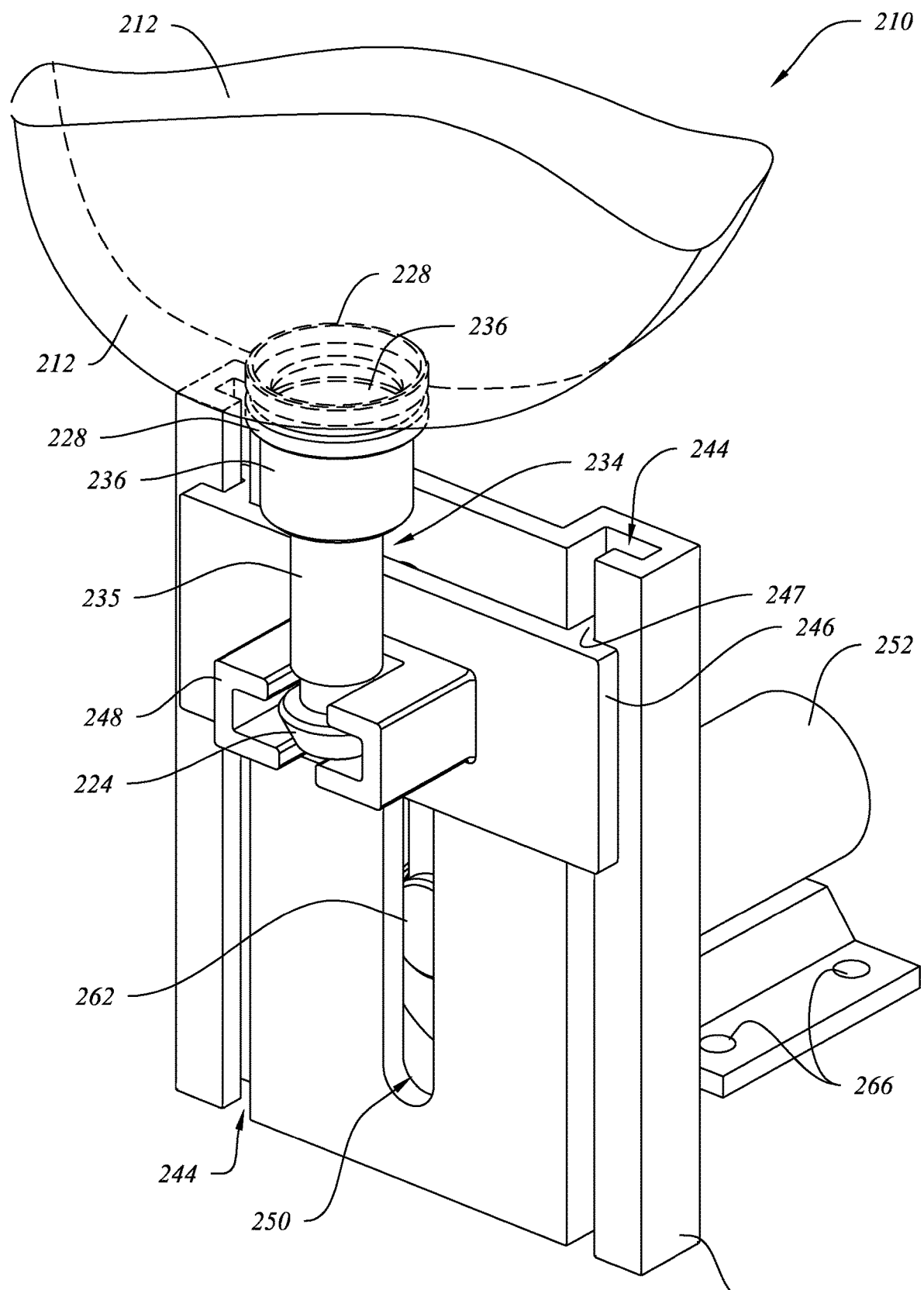
FIG. 4 is a front perspective view of another preferred embodiment of a delivery system according to the invention.
Figure 5:
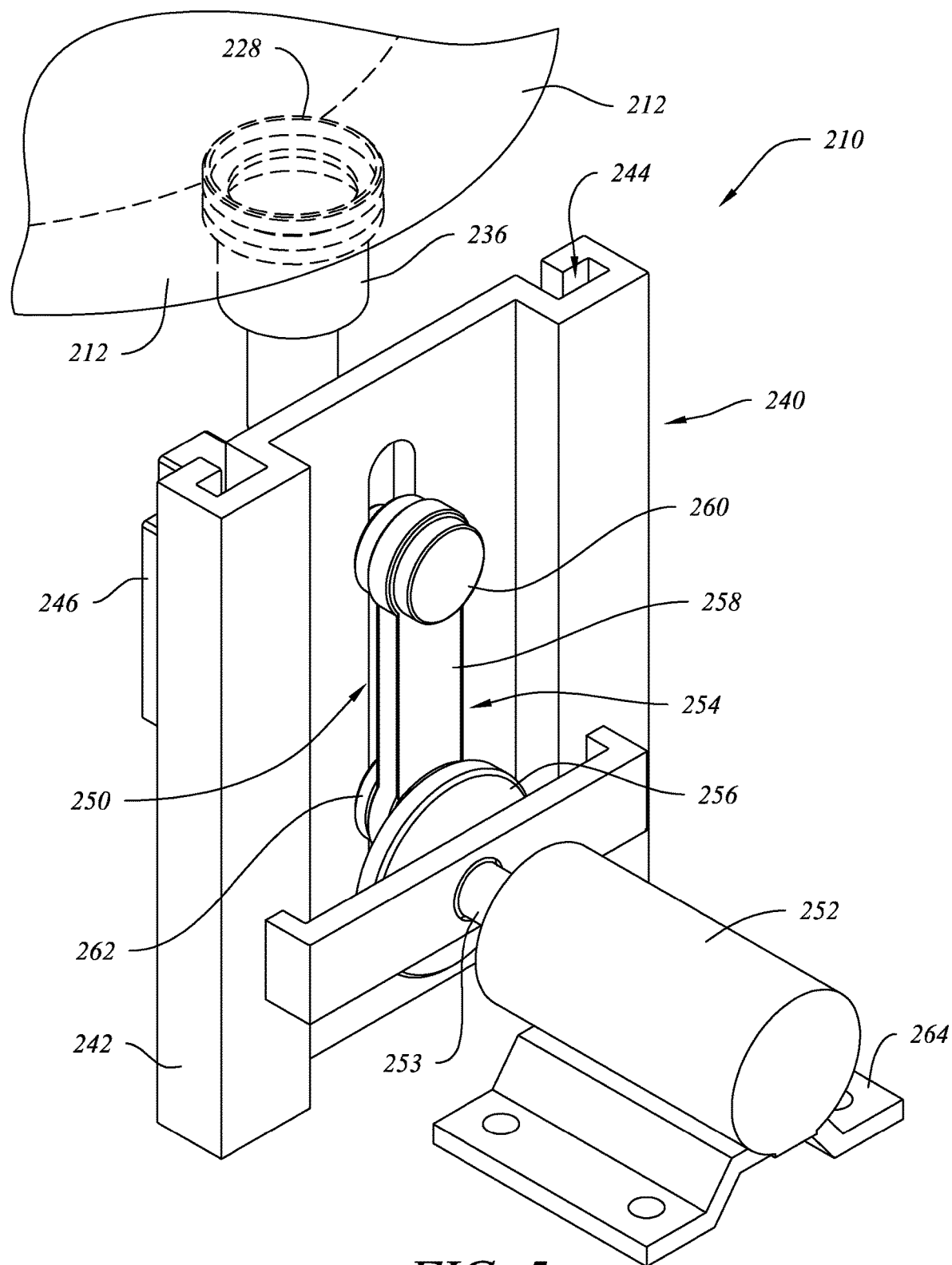
FIG. 5 is a rear perspective view of the embodiment of the delivery system of FIG. 4.
Figure 6:
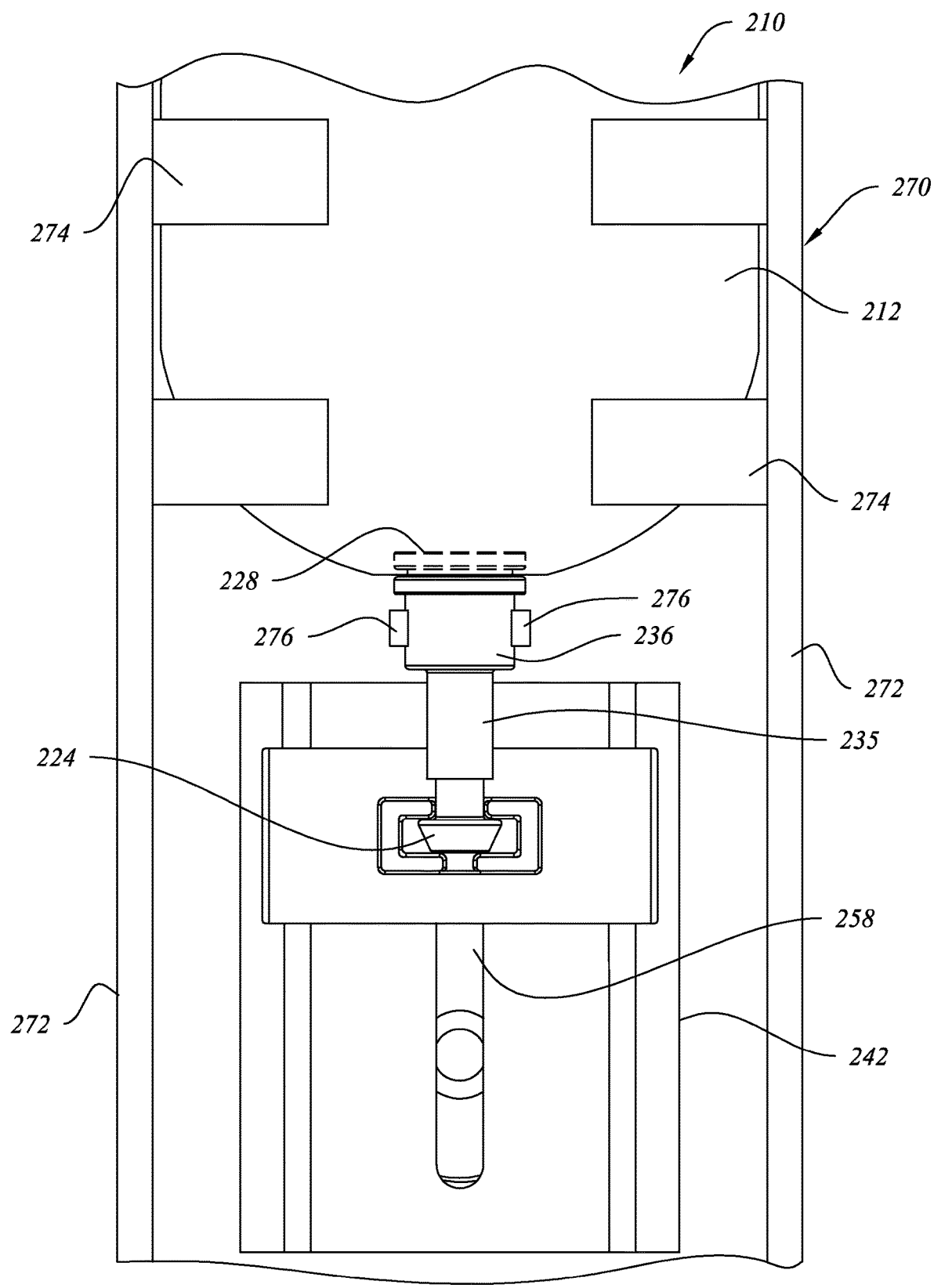
FIG. 6 is a partial front perspective view of the delivery system of FIG. 4 within a support housing.
Figure 7:
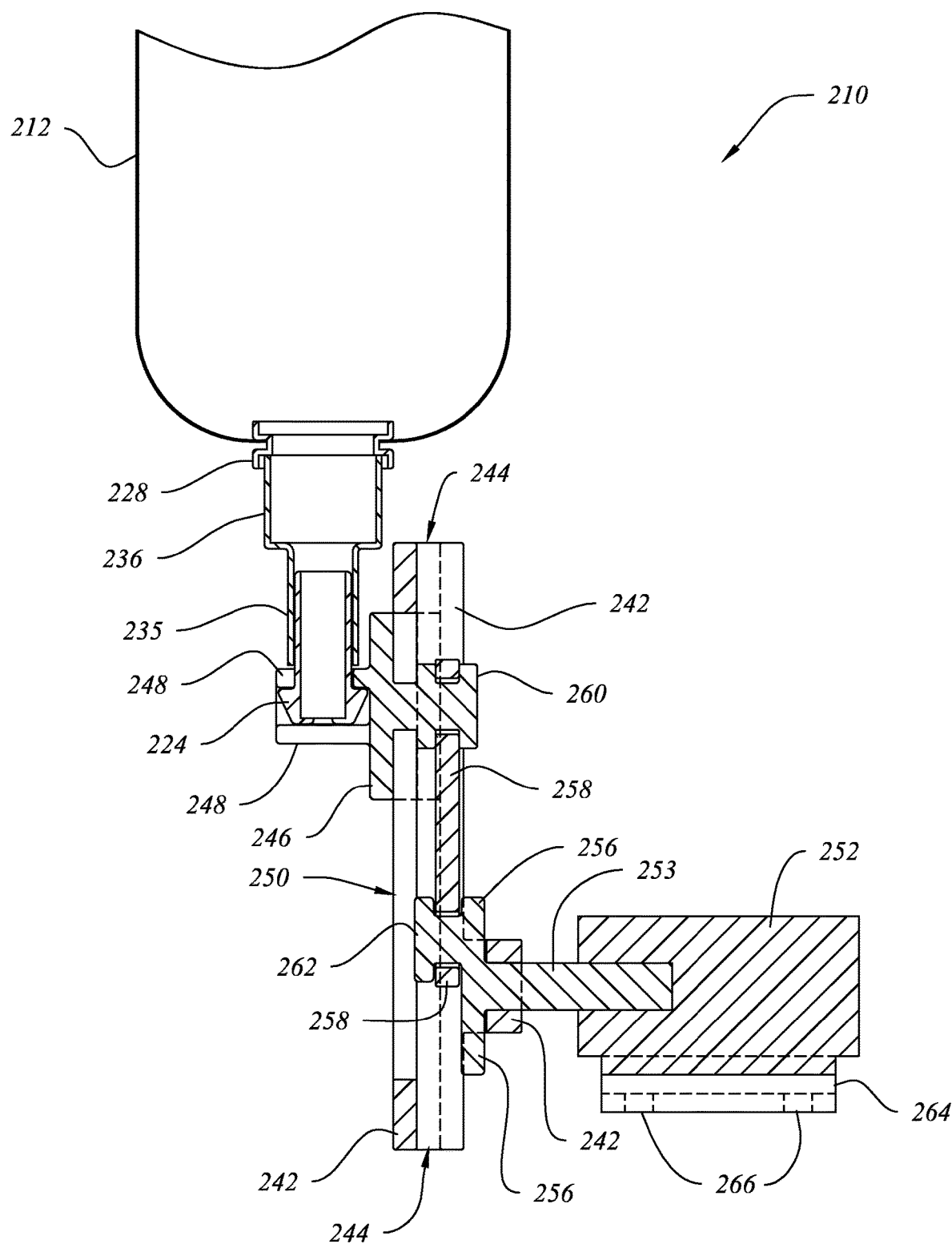
FIG. 7 is a side elevation cross-sectional view of the delivery system of FIG. 4.

As shown in FIG. 3, an alternate configuration for a container and tubing suitable for use with system 10, 110, or 210 (as discussed below) is shown. Container 212 comprises an integrally formed or pre-attached spout 228. Spout 228 is preferably sealed with a removable cap during shipping and storage. Spout 228 preferably has threads that mate with threads inside the cap so that it is easily removed when the probiotic composition inside container 212 is ready to be dispensed. Alternatively, spout 228 may have a removable seal or covering to seal-off container 212, without requiring the use of a cap. Tubing 215 preferably comprises an upper end 216 that comprises a connector 232 designed to mate with spout 228 to allow fluid communication between container 212 and tubing 215 through spout 228. Preferably, connector 232 comprises threads that mate with threads on spout 228. Prior to shipping, it is preferred that tubing 215 be sterilized, preferably by UV sterilization, and that both ends of tubing 215 be sealed to prevent contamination during shipping and storage. The seals would be removed when tubing 215 is attached to container 212 and ready to dispense the probiotic composition. Container 212 and tubing 215 may be used with the other parts of delivery systems 10, 110, or 210, depending on whether a pump-fed application or gravity-fed application is desired. The features previously described for tubing 15, such as a duck bill valve or spray nozzle, may also be used with tubing 215. Container 212 also preferably comprises an upper end 214 that forms a sealed-off section through which one or more holes 226 are provided to facilitate hanging container 212 from hooks or a nail at the site of consumption. Alternatively, container 212 may be hung from clips or similar mechanisms and upper end 214 may include externally protruding ridges to aid in securing container 212 to such clips.

As shown in FIGS. 4-7, another preferred embodiment of a delivery system 210 according to the invention is shown. Delivery system 210 is similar to delivery system 110 in that it relies on gravity to dispense the probiotic compositions or other fluids, rather than a pumping system. Delivery system 210 has the added benefit of allowing adjustment in the dosage volume using a piston-type valve actuated by a simple motor to vary the volume of dosing based on how long the motor is operated. Delivery system 210 preferably comprises a container 212, a metering valve 234, a valve mounting structure 240, a motor 252, a cam 254, and a motor mounting structure 264. Container 212 is similar to that shown in FIG. 3, but other containers and mechanisms for attaching the container used with system 210 to metering valve 234 and delivery tubing (similar to tubing 216) may be used. Container 212 is preferably hung at an elevated location, as discussed with respect to container 112 of system 110. Container 212 comprises a spout 228 that is connectable in fluid communication with metering valve 234. Metering valve 234 is preferably a capacity dosage piston system comprising an upper portion 236, a lower portion 235, and a piston 224. Upper portion 236 attaches to spout 228 to form a fluid tight seal. Upper portion 236 may comprise threads to mate with threads on spout 228 to connect the two parts together. The flow of fluid from container 212 is regulated by the piston 224, which is actuated by motor 252 and cam 254, as described below. Each pump stroke of piston 224 causes an amount of fluid from container 212 to be dispensed. Lower portion 235 is preferably configured to allow piston 224 to be inserted into the body of lower portion 235 and for sliding motion of piston 224 in and out of lower portion 235 as piston 224 is actuated by cam 254 to dispense an amount of fluid.

Valve mounting structure 240 preferably comprises a valve mounting base 242, a valve slider 246, and a piston bracket 248. Base 242 preferably comprises one or more slots 244 into which one or more corresponding protrusions 247 on valve slider 246 are inserted to attach valve slider 246 to base 244 in a slidable configuration. Piston bracket 248 is preferably connected to valve sider 246 and configured to mate with a portion of the body of piston 224, such that when valve slider 246 slides up or down relative to base 242, piston 224 correspondingly slides up or down relative to lower portion 235. The sliding motion of valve slider 246 is actuated by cam 254. Cam 254 preferably comprises a rotational body 256 and a shaft 258 disposed between and connected to rotational body 256 and first shaft connector 262 at one end and to a second shaft connector 260 at the other end. First shaft connector 262 allows shaft 258 to pivot as rotational body 256 rotates. Second shaft connector 260 connects cam shaft 258 to valve slider 246 through an elongated aperture 250 in valve mounting base 242. Cam 254 is connected to motor 252 by drive shaft 253. Motor 252 and drive shaft 253 drive rotational body 256 to rotate, which is translated into linear movement of valve slider 246 along the length of aperture 250 through cam shaft 258 and second shaft connector 260. As valve slider 246 moves up and down relative to mounting base 242, valve bracket 248 and consequently piston 224 are also moved up and down, which actuates opening or closing valve 234 to start or stop the flow of probiotic composition or other fluid from container 212. Tubing (similar to tubing 215, which may include all the features previously described for tubing 15) to carry the probiotic composition or other fluid from container 212 to the point of delivery, such as a water trough, is disposed through opening 249 in bracket 248, to allow fluid communication through valve 234 when valve 234 is in an open position.

Motor 252 is preferably a simple DC gear motor with an internal timing mechanism, but other types of motors may also be used. The timing mechanism activates the motor 252 to move piston 224 to open valve 234 for a predetermined amount of time and then activates the motor 252 again to close valve 234. Alternatively, the motor may run continuously for a period of time, repeatedly opening and closing the valve 234 until the desired dosage of fluid from container 212 is dispensed, then shut-off until the next predetermined cycle time. The cycle of opening and closing valve 234 would be periodically repeated, such as once every 24 hours, once every 8 hours, or any other selected cycle interval needed to dose the desired amount of probiotics or other fluid from container 212. Most preferably, the timing mechanism may be adjustable by a user or include multiple cycle timing options that may be selected by a user to achieve the desired activation and dosing schedule. Motor 252 may also be separately connected to a controller, similar to controller 122, and the various control mechanisms are the same as for controller 22 or 122. Other types of valves, such as a solenoid valve controlled by a programmable timer, may also be used with systems according to the invention to meter a dosage of fluid at given cycles to achieve a desired dosing rate.

Motor mounting structure 264 supports motor 252 and allows it to be securely attached to any suitable structure in the area where the fluid is to be discharged. One or more apertures 266 are preferably disposed through mounting structure 264 to allow it to be secured by screws or any conventional attachment mechanism. Most preferably, system 210 is disposed in a housing 270 and mounting structure 264 would be secured to an interior bottom wall of housing 270. Housing 270 is partially shown in FIG. 6. Housing 270 preferably comprises walls 272 on the sides, front, back, top and bottom surfaces, but the front, bottom and top walls are not shown in FIG. 6. Preferably either the front or top wall is a removable or openable door or cover to allow access to the interior of housing 270 to allow replacement of container 212 and other parts of the system 210 as needed. Housing 270 preferably comprises a plurality of support tabs 274 that extend inwardly from one or more walls 272, preferably from side walls 272, to aid in supporting and securing container 212 within housing 270. A spout retainer 276 is also preferably provided to allow insertion of spout 228 and to aid in supporting container 212 within housing. Hooks or clips may also be disposed on a top wall or near an upper end of a back wall of housing 270 to hang container 212 within housing 270 using holes 226 or by clipping onto upper end 214 of container 212. Housing 270 protects container 212 from inadvertent puncturing and could provide some protection for the motor 252 (or other type of controller) from the environmental conditions in the place of use. Most preferably, the containers and controllers used with system 10 and 110 are also preferably located within a cabinet or housing, such as housing 270 shown in FIG. 6, to provide additional protection for these components. Housing 270 or such other cabinet would preferably be located in an elevated position (particularly for systems 110 and 210, which rely on gravity feed) and securely attached to a wall or similar structure. Other parts of the systems 10, 110, or 210 may also be placed within housing 270 or such other cabinet.

Containers 12, 112, and 212 are designed to be discarded and replaced with new containers 12, 112, or 212 when the probiotic contents are all or substantially all consumed over the course of repeated dosing cycles. Preferably tubing 15 and 115 are pre-attached to the containers or integrally formed with the containers and are similarly discarded at the end of a container cycle. Tubing 215 is also preferably discarded and new tubing 215 used with each new container 212, but tubing 215 may be reused with a new container if desired. The size and volume of the feed container containing the probiotic composition, treatment composition or other sterile liquid may be scaled according to the use environment. Typically, containers 12, 112, or 212 will be sized to hold 1 liter to 25 liters of probiotic composition, treatment composition or other sterile liquid. Although dosing amounts may vary, depending on environmental conditions, type of feed mechanism used, and the type and number of animals involved, a one liter supply of probiotic composition according to the invention added to drinking water will be sufficient to provide an average pig with $5.4 \times 10^9$ spores per day for 30 days or could supply 2,000 chickens at a rate of $10^6$ spores per day per chicken for 50 days. This allows the use of smaller sized containers in most applications, which are easier to handle by a single person, but may require more frequent replacement with new containers to replenish the supply of probiotic composition. Larger sized containers may also be used and containers 12, 112, or 212 may be placed within a cabinet or other housing (such as housing 270 shown in FIG. 6) to help support the size and weight of the container or may be replaced within larger bottles or barrels as needed.

Systems 10, 110, and 210 may be used to dispense probiotic and/or synbiotic compositions to animal feed, drinking water, bedding or housing areas. When dispensed to bedding and housing areas, the probiotic composition spores might compete with pathogenic bacteria, and should degrade organic matter, thus reducing odors. Most preferably, systems 10, 110, and 210 are used to dispense probiotic and/or synbiotic compositions to animal drinking water. Frequently, the drinking water is dispensed in a trough with flowing water. The dispensing point at the end of tubing portion 18 or 118 or similar end of tubing 215 may be located at the head of the trough so that the probiotic composition may flow downstream to reach multiple animal drinking locations. Other components may be added to these systems which enhance the ability to control the feed of the probiotics. For example, a flow meter to proportion the probiotic feed rate to the water flow rate or a venturi to pull the probiotic composition proportional to the water flow rate may be used. When used with an individual, non-flowing water station, a water level sensor could be incorporated into the system. In combination with the controller, the water sensor could track the animal's water intake in order to determine the amount of probiotic ingested. This information could be used as part of an optimization program for animal husbandry. This type of system is also useful with household pets, which typically have individual water bowls. Those of ordinary skill in the art will understand the modifications need to incorporate such features.

With respect to system 10, the amount or rate of probiotic composition dispensed or fed will be a function of the rate of pumping, the duration of the pumping cycle, and the size of tubing used. With respect to system 110, the amount or rate of probiotic dispensed or fed will be a function of the duration the valve is opened, the head pressure, and the size of tubing used. With respect to system 210, the amount or rate of probiotic dispensed or fed will be a function of the number of pump strokes or the duration the valve is opened, the head pressure, and size of tubing used. The viscosity of the probiotic composition may also impact the amount or rate with which the composition is dispensed. The desirable doses of the probiotic compositions will vary depending on the probiotic used and the particular animal or plant species involved. For example, larger size or "finishing" pigs are generally regarded as requiring some of the highest doses of probiotics to be beneficial. A typical pig weighing between 145 and about 224 pounds will drink an average of 9 liters of water per day. A suggested dose of DFM *Bacillus* is around $5 \times 10^9$ cfu/pig/day/9 liters of water. A probiotic composition, such as one according to the invention, may provide around $5.5 \times 10^5$ cfu/mL to around $6.0 \times 10^5$ cfu/mL. Dosed out over a month, a one liter probiotic composition will provide around 32 mL/day and provide a spore count of around $6.0 \times 10^5$ cfu/mL or a total of $5.4 \times 10^9$ spores/day—the amount needed per pig. Therefore, a one liter supply will last around one month for a single pig in this weight range. Smaller pigs or chickens or other types of animals would typically require smaller doses of probiotics, which would make a one liter supply last longer or be sufficient to dose a larger number of animals. Various factors may alter these numbers, which are intended to be exemplary and not limiting. For example, when dispensed into a water trough with flowing water, the water flow-rate may also impact the dose that reaches each animal drinking from the trough. As animals grow, the desirable dose of probiotics will increase. Those of ordinary skill in the art will understand how to determine the desirable dose, and how to adjust the parameters of the systems of the invention in order to achieve those doses, so as to deliver an effective amount of probiotic composition to the animal or plant consuming the probiotic.

Although primarily described herein with respect to animal watering and feeding stations, the systems of the invention may also be used to deliver probiotics to plants by delivery to a planter or the soil around a plant, water tank or cistern, or to aquatic species, such as in a pond or fish tank. The systems of the invention are designed to be easily programmed and re-programmed at the point of consumption to adjust the amount of probiotic dispensed to achieve the desired doses of probiotics based on the variables present.

Generally, overdosing is not problematic for the animal or plant involved, but may result in wasting the probiotic composition, which increases the costs involved. Additionally, when used with the probiotic compositions of the invention, the bacteria should be able to survive for several hours once dispensed from the system, and may even germinate in the drinking water or pond or fish tank, if that is the point of consumption to which the probiotic is dispensed. While it is an object of the invention to provide a system and method that will efficiently maximize delivery of the probiotic composition to the intended animals or plants, rather than the compositions being wasted because they are not consumed before the bacteria are no longer viable, the timing of delivery and dosage amounts need not be precise.

Most preferably, systems 10, 110, and 210 are used to dispense probiotic and/or synbiotic compositions to animal drinking water in conjunction with acidified drinking water. As mentioned above, probiotic compositions according to the invention may include additional acidifiers that may be used to acidify water delivered to animals. Because the size of the probiotic containers are typically relatively small, using the container of probiotic composition to acidify the drinking water is feasible only in small scale situations involving a single, smaller sized trough or drinking station. When a larger scale watering system is used, it is preferred to have a separate acidification system to be used in conjunction with system 10, 110, or 210. Various acidizing products are commercially available, such as Vevo Vital, Acid LAC, Seiko-pH, Lupro-COD NA, and Amasil NA. Generally, they are used with a dosing/injection system, such as one commercially available from Dosatron.

Although commercially available acidifiers (which may contain a single acid or blend of acids or salts of acids) may be used in conjunction with system 10, 110, or 210, certain acids or salts of acids are preferred to be used to acidify the drinking water based on their antimicrobial activity. For example, acetic acid inhibits growth of *E. coli* and *Salmonella*; propionic acid and sorbic acid are antifungal (yeasts, molds) and have anti-bacterial activity with respect to *E. coli* (including ETEC), Coliforms, and *Salmonella*; lactic acid also has high anti-bacterial activity with respect to *E. coli* (including ETEC), Coliforms, and *Salmonella*, however it can be metabolized by many yeasts and molds; fumaric acid has anti-bacterial activity for *E. coli* (including ETEC), Coliforms, and *Clostridia*; citric and benzoic acids have anti-bacterial activity for *E. coli* (including ETEC) and Coliforms. Many common salts of these acids, such as calcium formate, calcium propionate, potassium diformate, potassium sorbate, sodium butyrate, sodium benzoate, and sodium formate, similarly have antimicrobial activity. Most preferably, the acids selected to acidify the drinking water have a pH value lower than the pKa value so that the undissociated form will be dominate. The undissociated form is desirable because it is able to penetrate the cell wall of the pathogenic bacteria, without negatively impacting the beneficial bacteria in the probiotic composition. Many of these acidifiers are included in the preferred list of preservatives or acidifiers used with probiotic compositions according to the invention. As will be understood by those of ordinary skill in the art, different dosing rates for acidifiers will be used, depending on the number, type, age, and size of animals, seasonal and environmental conditions (as animals will usually consume more water during periods of elevated temperatures and during daylight or simulated daylight hours). Most preferably, the water in the water system is tested to determine its pH before adding any acidifier and the amount of acidifier added is adjusted based on that base measurement. This avoids adding too much (which may be harmful to the animals and water system equipment) or too little acidifier (which eliminates the benefits to either or both the water system and animals). It is preferred that sufficient acids or salts of acids be added to the drinking water to achieve a pH in the range of about 4.5 to 6.5, most preferably between about 4.5 to 5.0.

An additional benefit of DFM using compositions according to the invention is that many of the *Bacillus* species, will survive through the intestinal tract and remain viable in feces as either spores or vegetative forms. Having these beneficial bacteria in the feces aids in reducing odors associated with the animal waste products. Although treatment compositions containing bacteria may be directly applied to animal waste, such as manure piles, housing and bedding to reduce odors, a problem frequently encountered is that it may be difficult to adequately and evenly distribute the bacterial treatment over the surfaces having substances that produce the odors, and particularly to distribute the bacterial treatment through a pile of manure. Having the treatment bacteria in the feces of the animal through a DFM application aids in evenly distributing the beneficial bacteria throughout the feces and throughout manure piles or storage facilities.

Those of ordinary skill in the art will also appreciate upon reading this specification, that modifications and alterations to the probiotic compositions and methodology and system for delivery of probiotic compositions may be made within the scope of the invention and it is intended that the scope of the invention disclosed herein be limited only by the broadest interpretation of the appended claims to which the inventors are legally entitled.

We claim:

1. An orally ingestible probiotic suspension composition for treating animals, the composition comprising:
    water;
    one or more of *Bacillus pumilus, Bacillus licheniformis, Bacillus amylophilus, Bacillus subtilis, Bacillus clausii, Bacillus firmus, Bacillus megaterium, Bacillus mesentericus, Bacillus subtilis* var. *natto*, or *Bacillus toyonensis* in spore form;
    one or more of citric, benzoic, sorbic, fumaric, or propionic acids or salts of these acids; and
    a thickener;
    wherein the composition comprises less than 1% total of the one or more acids or salts of acids by weight of the composition;
    wherein the composition has a pH between 4.5 and 5.5; and
    wherein all ingredients in the composition meet U.S. federal GRAS standards and the composition is storage stable with the bacteria remaining in spore form during storage for at least one month.

2. The probiotic composition according to claim 1 wherein the composition has a pH of 4.5 to 4.7.

3. The probiotic composition of claim 1 wherein the thickener is one or more of xanthan gum, acacia gum, locust bean gum, guar gum or gum arabic.

4. The probiotic composition of claim 1 wherein the composition is a liquid comprising bacteria spore counts of around $1.0 \times 10^8$ to $1.0 \times 10^{10}$ cfu/mL of composition, about 0.1 to 5.0% by weight thickener, and 0.05 to 0.5% by weight total of the one or more acids or salts of acids.

5. The probiotic composition of claim 4 comprising two or more of citric, benzoic, sorbic, fumaric, or propionic acids or salts of these acids.

6. The probiotic composition of claim 5 wherein the bacteria are in a bacteria spore blend comprising 40% to 60% sodium chloride and 60%-40% of the one or more *Bacillus* species in spore form, the percentages being by total weight of the bacteria spore blend.

7. The probiotic composition of claim 1 further comprising a surfactant.

8. The probiotic composition of claim 7 wherein the surfactant is polysorbate 80.

9. The probiotic composition of claim 4 further comprising a water activity reducer.

10. The probiotic composition of claim 9 wherein the water activity reducer is one or more of sodium chloride, potassium chloride, or a 70% corn syrup solution.

11. The probiotic composition of claim 1 further comprising around 0.1 to 0.3% by weight potassium chloride.

12. The probiotic composition according to claim 1 wherein the thickener is a prebiotic.

13. The probiotic composition of claim 1 wherein the bacteria are in a bacteria spore blend comprising 40%-60% sodium chloride and 60%-40% of the one or more *Bacillus* species in spore form, the percentages being by total weight of the bacteria spore blend.

14. The probiotic composition according to claim 7 wherein all ingredients in the composition are homogenously mixed and the bacteria spores are suspended in the composition.

15. The probiotic composition according to claim 1 wherein the bacteria comprises one or more of *Bacillus amylophilus, Bacillus mesentericus*, or *Bacillus toyonensis* in spore form.

16. The probiotic composition according to claim 1 wherein the acids or salts of acids comprise:
    citric acid;
    benzoic acid or sodium benzoate; and
    sorbic acid or potassium sorbate.

17. The probiotic composition according to claim 13 comprising:
    around 0.01% to 10% of the bacteria spore blend
    around 0.1-0.33% sorbic acid, its salt, or a combination thereof;
    around 0.1-0.34% citric acid, its salt, or a combination thereof;
    around 0.1-0.33% benzoic acid, its salt, or a combination thereof;
    around 0.2-0.5% xanthan gum;
    around 0.00005% to 3.0% of a surfactant; and
    around 0.1-0.3% sodium chloride, potassium chloride, or a combination thereof, all percentages by weight of the composition.

18. The probiotic composition according to claim 17 wherein the total of the acids or their salts is 0.5% or less.

19. The probiotic composition according to claim 13 wherein the spore blend comprises around $2 \times 10^8$ to $2 \times 10^{11}$ spores per gram of *Bacillus subtilis* and *Bacillus licheniformis* strains in spore form.

20. The probiotic composition according to claim 13 wherein the composition comprises around 0.01% to 10% of the bacteria spore blend.

21. The probiotic composition according to claim 20 wherein the spores are spray dried from a liquid fermentation concentrate and wherein the composition further comprises a surfactant.

22. An orally ingestible probiotic suspension composition for treating animals, the composition consisting of:
    1% to 10% of a bacteria spore blend containing salt and one or more of *Bacillus pumilus, Bacillus licheniformis, Bacillus amylophilus, Bacillus subtilis, Bacillus clausii, Bacillus firmus, Bacillus megaterium, Bacillus mesentericus, Bacillus subtilis* var. *natto*, or *Bacillus toyonensis* in spore form;
    0.3% to 1% total of one or more acids or salts of acids; and
    0.2% to 0.5% of a thickener;
    0.1-0.3% sodium chloride, potassium chloride, or a combination thereof;
    0.00005% to 3.0% of a surfactant; and
    86.2% to 98.4% water;
    wherein the composition has a pH between 4.5 and 5.5;
    wherein all ingredients in the composition meet federal GRAS standards; and
    wherein all percentages are by weight of the composition.

23. The orally ingestible probiotic suspension of claim 22 wherein the acids or salts of acids are two or more of citric, benzoic, sorbic, fumaric, or propionic acids or salts of these acids.

24. The orally ingestible probiotic suspension of claim 22 wherein the composition comprises 0.1-0.33% sorbic acid, its salt, or a combination thereof; 0.1-0.34% citric acid, its salt, or a combination thereof; and 0.1-0.33% benzoic acid, its salt, or a combination thereof;
    wherein the thickener is xanthan gum; and
    wherein the surfactant is polysorbate 80.

25. The orally ingestible probiotic suspension of claim 22 wherein the bacteria spore blend contains salt, one or more strains of *Bacillus licheniformis* in spore form, and one or more strains of *Bacillus subtilis* in spore form.

26. The probiotic composition according to claim 22 wherein the composition has a pH of 4.5 to 4.7.

27. The probiotic composition of claim 1 wherein the composition comprises at least two acids or salts of acids and wherein at least one of those acids or salts of acids is sorbic acid or a salt of sorbic acid or benzoic acid or a salt of benzoic acid.

28. The probiotic composition of claim 22 wherein at least some of the bacteria remain in a spore state until the composition is ingested by an animal.

29. The probiotic composition of claim 1 wherein at least some of the bacteria remain viable as spores or in a vegetative state in feces of the animal after the composition is ingested.

30. The probiotic composition of claim 1 wherein the composition is storable for up to two months at a temperature between 39° F.-95° F. without any settling or layering of ingredients and with spore counts that are comparable to the counts when the composition is initially made.

31. The probiotic composition of claim 30 wherein the composition is storable for up to two months at a temperature between 39° F.-46° F. without any settling or layering of ingredients and with spore counts that are comparable to the counts when the composition is initially made.

32. The probiotic composition of claim 19 wherein the composition is storable for up to two months at a temperature between 39° F.-95° F. without any settling or layering of ingredients and with spore counts that are comparable to the counts when the composition is initially made.

* * * * *